US006852508B1

(12) United States Patent
Herrmann et al.

(10) Patent No.: US 6,852,508 B1
(45) Date of Patent: Feb. 8, 2005

(54) CHEMOKINE WITH AMINO-TERMINAL MODIFICATIONS

(75) Inventors: Stephen H. Herrmann, Wellesley, MA (US); Zhijian Lu, Bedford, MA (US); John M. McCoy, Reading, MA (US); Stephen L. Swanberg, Boston, MA (US); Bruce Walker, Charlestown, MA (US); Otto Yang, Charlestown, MA (US)

(73) Assignees: Genetics Institute, LLC, Cambridge, MA (US); The General Hospital Corporation, Boston, MA (US)

( * ) Notice: Subject to any disclaimer, the term of this patent is extended or adjusted under 35 U.S.C. 154(b) by 681 days.

(21) Appl. No.: 09/175,713

(22) Filed: Oct. 20, 1998

Related U.S. Application Data

(63) Continuation-in-part of application No. 08/808,720, filed on Feb. 28, 1997, now Pat. No. 6,100,387.
(60) Provisional application No. 60/113,672, filed on Oct. 22, 1997.

(51) Int. Cl.$^7$ .................. C12P 21/06; C07H 21/04; C07H 14/00; A61K 38/00
(52) U.S. Cl. ............... 435/69.1; 536/23.5; 530/324; 514/2
(58) Field of Search ............... 536/23.5; 435/69.1; 530/324; 514/2

(56) References Cited

U.S. PATENT DOCUMENTS

| | | | |
|---|---|---|---|
| 4,235,871 A | 11/1980 | Papahandjopoulos et al. | |
| 4,501,728 A | 2/1985 | Geho et al. | |
| 4,518,584 A | 5/1985 | Mark et al. | |
| 4,737,323 A | 4/1988 | Martin et al. | |
| 4,837,028 A | 6/1989 | Allen | |
| 5,270,181 A | 12/1993 | McCoy et al. | |
| 5,292,464 A | 3/1994 | McCoy et al. | |
| 5,563,048 A | 10/1996 | Honjo et al. | |
| 5,580,754 A | 12/1996 | Samal | |
| 5,605,817 A | 2/1997 | Coleman et al. | |
| 5,616,688 A | 4/1997 | Cerami et al. | |
| 5,627,156 A * | 5/1997 | Talmadge ............... | 514/13 |
| 5,650,150 A | 7/1997 | Gillies | |
| 6,080,398 A * | 6/2000 | Pelus et al. ............ | 424/85.1 |

FOREIGN PATENT DOCUMENTS

| | | |
|---|---|---|
| EP | 0 699 766 A | 3/1996 |
| EP | 0 763 543 A2 | 3/1997 |
| EP | 0 816 510 A1 | 1/1998 |
| WO | WO 95/21258 | 8/1995 |
| WO | WO 96/04388 | 2/1996 |
| WO | WO 96/13587 | 5/1996 |
| WO | WO 96-17935 | 6/1996 |
| WO | WO 96/23888 A | 8/1996 |
| WO | WO 96/34819 | 11/1996 |
| WO | WO 96/38559 | 12/1996 |
| WO | WO 96/39520 | 12/1996 |
| WO | WO 96/39521 | 12/1996 |
| WO | WO 96/39522 | 12/1996 |
| WO | WO 96/40762 | 12/1996 |
| WO | WO 96/40786 | 12/1996 |
| WO | WO 97/00691 | 1/1997 |
| WO | WO 97/19173 | 5/1997 |
| WO | WO 97/34631 A1 | 9/1997 |
| WO | WO 94/29341 | 12/1997 |
| WO | WO 98/04698 A1 | 2/1998 |

OTHER PUBLICATIONS

Proudfoot et al., J. Bio. Chem. vol. 271, 2599–2603, 1996.*
U.S. Appl. No. 08/165,301, filed Dec. 10, 1993, McCoy et al.
U.S. Appl. No. 08/535,116, filed Oct. 11, 1995.
U.S. Appl. No. 08/595,590, filed Feb. 2, 1996, Gray et al.
U.S. Appl. No. 08/810,436, filed Mar. 4, 1997, McCoy et al.
Kaufman et al., Nucleic Acids Res 19:4485–4490 (1991).
Kaufman, Methods in Enzmology 185:537–566 (1990).
Current Protocols in Immunology, Ed. by J.E. Coligan, A.M. Kruisbeek, D. H. Margulier, E.M. Shevach, W. Strober, Pub. by Green Publishing Associates and Wiley–Interscience (Chapter 6.12, Measurement of alpha and beta Chemokines 6.12,1–6.12.28.
Baub et al. J. Clin. Invest. 95:1370–1376, 1995.
Lind et al. APMIS 103:140–146, 1995.
Muller et al. Eur. J. Immunol. 25:1744–1748.
Gruber et al, J. of Immunol. 153: 1762–1768, 1994.
Johnston et al., J, of Immunol. 153.1762–1768, 1994.
Saragovi et al. Bio/Technology 10, 773–778 (1992).
McDowell, et al. J. Amer. Chem. Soc. 114 9245–9253 (1992).
Current Protocols in Immunology, edited by J.E. Coligan, A.M. Kruisbeek, D. H. Margulier, E.M. Shevach, W. Strober, Pub. by Green Publishing Associates and Wiley-Interscience (Chapter 7.28, Measurement of Cellular Adhesion under static conditions 7 28. 1–7, 28 22).
Takai et al. Proc. Natl Acad. Sci. USA 84.6864–6868. 1987.
Bierer et al. J. Exp. Med 168:1145–1156.1988.
Rosenstein et al. J. Exp. Med. 169:149–160 1989.
Stoltenbert et al. J. Immunol. Methods 175–59–68.1994.
Stitt et al; Cell 80:661–670. 1995.
Merrifield, J. Amer. Chem Soc 85 2149–2154 (1963).
Krstenansky et al. REBS Lett, 211, 10 (1987).
Arenzana–Seisdedos et al. Nature 383:400 (1996).
Bates, P., Cell 86: 1–3 (1996).
Bates, C.C. et al., J. Exp. Med. 184: 1101–1109 (1996).
Cocchi, F. et al. Science 270: 1811–1815 (1995).
Dragic, T. et al., Nature 381: 667–673 (1996).
J nsson, U. et al., Bio Techniques 11:620–627 (1991).
Mackay, C. R. J. Exp. Med. 184:799–802 (1996).

(List continued on next page.)

*Primary Examiner*—Janet L. Andres
(74) *Attorney, Agent, or Firm*—Jenkens & Gilchrist, P.C.

(57) ABSTRACT

This invention provides polynucleotides comprising sequences encoding amino-terminal-modified chemokines, the encoded amino-terminal-modified chemokines, and uses thereof.

4 Claims, 2 Drawing Sheets

OTHER PUBLICATIONS

Nagasawa, T. et al., nature 382:635–638 (1996).
Nagasawa, T. et al., Proc. Natl. Acad Sci. USA 91:2305–2309 (1994).
Oberlin, E. et al., Nature 382:833–835 (1996).
Schmidtmayerova, H. et al., Nature 382:767 (1996).
Seachrist, L., BioWorld Today 8 (23): 1,4 (1997).
Tashiro K. et al. Science 261: 600–603 (1993).
Wells, T.N.C. et al., Annals of the New York academy of Sciences, 796: 245–246 (1996).
Wu, L. et al., Nature 384: 179–183 (1996).
Howard et al., Trends in Biochemistry 14: 46–51, Feb. 1996.

* cited by examiner

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 89 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:1:

```
Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80
```

Glu Tyr Leu Glu Lys Ala Leu Asn Lys
                        85

(2) INFORMATION FOR SEQ ID NO:2:

(i) SEQUENCE CHARACTERISTICS:
        (A) LENGTH: 93 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

(2) INFORMATION FOR SEQ ID NO:3:

(i) SEQUENCE CHARACTERISTICS:
        (A) LENGTH: 1856 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

| | | | | | |
|---|---|---|---|---|---|
| TCTCCGTCAG | CCGCATTGCC | CGCTCGGCGT | CCGGCCCCCG | ACCCGTGCTC | GTCCGCCCGC | 60 |
| CCGCCCGCCC | GCCCGCGCCA | TGAACGCCAA | GGTCGTGGTC | GTGCTGGTCC | TCGTGCTGAC | 120 |
| CGCGCTCTGC | CTCAGCGACG | GGAAGCCCGT | CAGCCTGAGC | TACAGATGCC | CATGCCGATT | 180 |
| CTTCGAAAGC | CATGTTGCCA | GAGCCAACGT | CAAGCATCTC | AAAATTCTCA | ACACTCCAAA | 240 |
| CTGTGCCCTT | CAGATTGTAG | CCCGGCTGAA | GAACAACAAC | AGACAAGTGT | GCATTGACCC | 300 |
| GAAGCTAAAG | TGGATTCAGG | AGTACCTGGA | GAAAGCTTTA | AACAAGTAAG | CACAACAGCC | 360 |
| AAAAAGGACT | TTCCGCTAGA | CCCACTCGAG | GAAAACTAAA | ACCTTGTGAG | AGATGAAAGG | 420 |
| GCAAAGACGT | GGGGGAGGGG | GCCTTAACCA | TGAGGACCAG | GTGTGTGTGT | GGGGTGGGCA | 480 |
| CATTGATCTG | GGATCGGGCC | TGAGGTTTGC | AGCATTTAGA | CCCTGCATTT | ATAGCATACG | 540 |
| GTATGATATT | GCAGCTTATA | TTCATCCATG | CCCTGTACCT | GTGCACGTTG | AACTTTTAT | 600 |
| TACTGGGGTT | TTTCTTAGAA | AGAAATTGTA | TTATCAACAG | CATTTTCAAG | CAGTTAGTTC | 660 |
| CTTCATGATC | ATCACAATCA | TCATCATTCT | CATTCTCATT | TTTTAAATCA | ACGAGTACTT | 720 |
| CAAGATCTGA | ATTTGGCTTG | TTTGGAGCAT | CTCCTCTGCT | CCCCTGGGGA | GTCTGGGCAC | 780 |
| AGTCAGGTGG | TGGCTTAACA | GGGAGCTGGA | AAAAGTGTCC | TTTCTTCAGA | CACTGAGGCT | 840 |
| CCCGCAGCAG | CGCCCCTCCC | AAGAGGAAGG | CCTCTGTGGC | ACTCAGATAC | CGACTGGGGC | 900 |
| TGGGGCGCCG | CCACTGCCTT | CACCTCCTCT | TTCAAACCTC | AGTGATTGGC | TCTGTGGGCT | 960 |

```
CCATGTAGAA GCCACTATTA CTGGGACTGT CTCAGAGACC CCTCTCCCAG CTATTCCTAC    1020

TCTCTCCCCG ACTCCGAGAG CATGCTTAAT CTTGCTTCTG CTTCTCATTT CTGTAGCCTG    1080

ATCAGCGCCG CACCAGCCGG GAAGAGGGTG ATTGCTGGGG CTCGTGCCCT GCATCCCTCT    1140

CCTCCCAGGG CCTGCCCCAC AGCTCGGGCC CTCTGTGAGA TCCGTCTTTG GCCTCCTCCA    1200

GAATGGAGCT GGCCCTCTCC TGGGGATGTG TAATGGTCCC CCTGCTTACC CGCAAAAGAC    1260

AAGTCTTTAC AGAATCAAAT GCAATTTTAA ATCTGAGAGC TCGCTTGAGT GACTGGGTTT    1320

GTGATTGCCT CTGAAGCCTA TGTATGCCAT GGAGGCACTA ACAAACTCTG AGGTTTCCGA    1380

AATCAGAAGC GAAAAAATCA GTGAATAAAC CATCATCTTG CCACTACCCC CTCCTGAAGC    1440

CACAGCAGGG GTTCAGGTTC AATCAGAAC TGTTGGCAAG GTGACATTTC CATGCATAGA     1500

TGCGATCCAC AGAAGGTCCT GGTGGTATTT GTAACTTTTT GCAAGGCATT TTTTTATATA    1560

TATTTTTGTG CACATTTTTT TTTACGATTC TTTAGAAAAC AAATGTATTT CAAAATATAT    1620

TTATAGTCGA ACAAGTCATA TATATGAATG AGAGCCATAT GAATGTCAGT AGTTTATACT    1680

TCTCTATTAT CTCAAACTAC TGGCAATTTG TAAAGAAATA TATATGATAT ATAAATGTGA    1740

TTGCAGCTTT TCAATGTTAG CCACAGTGTA TTTTTTCACT TGTACTAAAA TTGTATCAAA    1800

TGTGACATTA TATGCACTAG CAATAAAATG CTAATTGTTT CATGGTAAAA AAAAAA       1856
```

(2) INFORMATION FOR SEQ ID NO:4:

(i) SEQUENCE CHARACTERISTICS:
        (A) LENGTH: 3526 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

```
TCTCCGTCAG CCGCATTGCC CGCTCGGCGT CCGGCCCCCG ACCCGTGCTC GTCCGCCCGC      60

CCGCCCGCCC GCCCGCGCCA TGAACGCCAA GGTCGTGGTC GTGCTGGTCC TCGTGCTGAC     120

CGCGCTCTGC CTCAGCGACG GGAAGCCCGT CAGCCTGAGC TACAGATGCC CATGCCGATT     180

CTTCGAAAGC CATGTTGCCA GAGCCAACGT CAAGCATCTC AAAATTCTCA ACACTCCAAA     240

CTGTGCCCTT CAGATTGTAG CCCGGCTGAA GAACAACAAC AGACAAGTGT GCATTGACCC     300

GAAGCTAAAG TGGATTCAGG AGTACCTGGA GAAAGCTTTA AACAAGAGGT TCAAGATGTG     360

AGAGGGTCAC ACGCCTGAGG AACCCTTACA GTAGGAGCCC AGCTCTGAAA CCAGTGTTAG     420

GGAAGGGCCT GCCACAGCCT CCCCTGCCAG GGCAGCGCCC CAGGCATTGC CAAGGGCTTT     480

GTTTTGCACA CTTTGCCATA TTTTCACCAT TTGATTATGT AGCAAAATAC ATGACATTTA     540

TTTTTCATTT AGTTTGATTA TTCAGTGTCA CTGGCGACAC GTAGCAGCTT AGACTAAGGC     600

CATTATTGTA CTTGCCTTAT TAGAGTGTCT TTCCACGGAG CCACTCCTCT GACTCAGGGC     660

TCCTGGGTTT TGTATTCTCT GAGCTGTGCA GGTGGGGAGA CTGGGCTGAG GGAGCCTGGC     720

CCCATGGTCA GCCCTAGGGT GGAGAGCCAC CAAGAGGGAC GCCTGGGGGT GCCAGGACCA     780

GTCAACCTGG GCAAAGCCTA GTGAAGGCTT CTCTCTGTGG GATGGGATGG TGGAGGGCCA     840

CATGGGAGGC TCACCCCCTT CTCCATCCAC ATGGGAGCCG GTCTGCCTC TTCTGGGAGG     900

GCAGCAGGGC TACCCTGAGC TGAGGCAGCA GTGTGAGGCC AGGGCAGAGT GAGACCCAGC     960

CCTCATCCCG AGCACCTCCA CATCCTCCAC GTTCTGCTCA TCATTCTCTG TCTCATCCAT    1020

CATCATGTGT GTCCACGACT GTCTCCATGG CCCCGCAAAA GGACTCTCAG GACCAAAGCT    1080
```

```
TTCATGTAAA CTGTGCACCA AGCAGGAAAT GAAAATGTCT TGTGTTACCT GAAAACACTG   1140

TGCACATCTG TGTCTTGTGT GGAATATTGT CCATTGTCCA ATCCTATGTT TTTGTTCAAA   1200

GCCAGCGTCC TCCTCTGTGA CCAATGTCTT GATGCATGCA CTGTTCCCCC TGTGCAGCCG   1260

CTGAGCGAGG AGATGCTCCT TGGGCCCTTT GAGTGCAGTC CTGATCAGAG CCGTGGTCCT   1320

TTGGGGTGAA CTACCTTGGT TCCCCCACTG ATCACAAAAA CATGGTGGGT CCATGGGCAG   1380

AGCCCAAGGG AATTCGGTGT GCACCAGGGT TGACCCCAGA GGATTGCTGC CCCATCAGTG   1440

CTCCCTCACA TGTCAGTACC TTCAAACTAG GGCCAAGCCC AGCACTGCTT GAGGAAAACA   1500

AGCATTCACA ACTTGTTTTT GGTTTTTAAA ACCCAGTCCA CAAAATAACC AATCCTGGAC   1560

ATGAAGATTC TTTCCCAATT CACATCTAAC CTCATCTTCT TCACCATTTG GCAATGCCAT   1620

CATCTCCTGC CTTCCTCCTG GGCCCTCTCT GCTCTGCGTG TCACCTGTGC TTCGGGCCCT   1680

TCCCACAGGA CATTTCTCTA AGAGAACAAT GTGCTATGTG AAGAGTAAGT CAACCTGCCT   1740

GACATTTGGA GTGTTCCCCT CCCACTGAGG GCAGTCGATA GAGCTGTATT AAGCCACTTA   1800

AAATGTTCAC TTTTGACAAA GGCAAGCACT TGTGGGTTTT TGTTTTGTTT TTCATTCAGT   1860

CTTACGAATA CTTTTGCCCT TTGATTAAAG ACTCCAGTTA AAAAAAATTT TAATGAAGAA   1920

AGTGGAAAAC AAGGAAGTCA AGCAAGGAA ACTATGTAAC ATGTAGGAAG TAGGAAGTAA    1980

ATTATAGTGA TGTAATCTTG AATTGTAACT GTTCGTGAAT TTAATAATCT GTAGGGTAAT   2040

TAGTAACATG TGTTAAGTAT TTTCATAAGT ATTTCAAATT GGAGCTTCAT GGCAGAAGGC   2100

AAACCCATCA ACAAAAATTG TCCCTTAAAC AAAAATTAAA ATCCTCAATC CAGCTATGTT   2160

ATATTGAAAA AATAGAGCCT GAGGGATCTT TACTAGTTAT AAAGATACAG AACTCTTTCA   2220

AAACCTTTTG AAATTAACCT CTCACTATAC CAGTATAATT GAGTTTTCAG TGGGCAGTC    2280

ATTATCCAGG TAATCCAAGA TATTTTAAAA TCTGTCACGT AGAACTTGGA TGTACCTGCC   2340

CCCAATCCAT GAACCAAGAC CATTGAATTC TTGGTTGAGG AAACAAACAT GACCCTAAAT   2400

CTTGACTACA GTCAGGAAAG GAATCATTTC TATTTCTCCT CCATGGGAGA AAATAGATAA   2460

GAGTAGAAAC TGCAGGGAAA ATTATTTGCA TAACAATTCC TCTACTAACA ATCAGCTCCT   2520

TCCTGGAGAC TGCCCAGCTA AAGCAATATG CATTTAAATA CAGTCTTCCA TTTGCAAGGG   2580

AAAAGTCTCT TGTAATCCGA ATCTCTTTTT GCTTTCGAAC TGCTAGTCAA GTGCGTCCAC   2640

GAGCTGTTTA CTAGGGATCC CTCATCTGTC CCTCCGGGAC CTGGTGCTGC CTCTACCTGA   2700

CACTCCCTTG GGCTCCCTGT AACCTCTTCA GAGGCCCTCG CTGCCAGCTC TGTATCAGGA   2760

CCCAGAGGAA GGGGCCAGAG GCTCGTTGAC TGGCTGTGTG TTGGGATTGA GTCTGTGCCA   2820

CGTGTATGTG CTGTGGTGTG TCCCCCTCTG TCCAGGCACT GAGATACCAG CGAGGAGGCT   2880

CCAGAGGGCA CTCTGCTTGT TATTAGAGAT TACCTCCTGA GAAAAAGCT TCCGCTTGGA    2940

GCAGAGGGGC TGAATAGCAG AAGGTTGCAC CTCCCCCAAC CTTAGATGTT CTAAGTCTTT   3000

CCATTGGATC TCATTGGACC CTTCCATGGT GTGATCGTCT GACTGGTGTT ATCACCGTGG   3060

GCTCCCTGAC TGGGAGTTGA TCGCCTTTCC CAGGTGCTAC ACCCTTTTCC AGCTGGATGA   3120

GAATTTGAGT GCTCTGATCC CTCTACAGAG CTTCCCTGAC TCATTCTGAA GGAGCCCCAT   3180

TCCTGGGAAA TATTCCCTAG AAACTTCCAA ATCCCCTAAG CAGACCACTG ATAAAACCAT   3240

GTAGAAAATT TGTTATTTTG CAACCTCGCT GGACTCTCAG TCTCTGAGCA GTGAATGATT   3300

CAGTGTTAAA TGTGATGAAT ACTGTATTTT GTATTGTTTC AAGTGCATCT CCCAGATAAT   3360

GTGAAAATGG TCCAGGAGAA GGCCAATTCC TATACGCAGC GTGCTTTAAA AAATAAATAA   3420

GAAACAACTC TTTGAGAAAC AACAATTTCT ACTTTGAAGT CATACCAATG AAAAAATGTA   3480
```

-continued

```
TATGCACTTA TAATTTTCCT AATAAAGTTC TGTACTCAAA TGTAAA                3526
```

(2) INFORMATION FOR SEQ ID NO:5:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Ala Ala Lys Asp Val Lys His His His His His His Gly Ser Gly Ser
1               5                  10                  15

Asp Asp Asp Asp Lys
        20
```

(2) INFORMATION FOR SEQ ID NO:6:

(i) SEQUENCE CHARACTERISTICS:
        (A) LENGTH: 207 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA construct"

(xi) SEQUENCE DESCRIPTION: SEQ ID NO:6:

```
ATGAAACCAG TATCTCTGTC TTATCGTTGT CCATGCCGAT TCTTCGAAAG CCATGTTGCC     60

AGAGCCAACG TCAAGCATCT CAAAATTCTC AACACTCCAA ACTGTGCCCT TCAGATTGTA    120

GCCCGGCTGA AGAACAACAA CAGACAAGTG TGCATTGACC CGAAGCTAAA GTGGATTCAG    180

GAGTACCTGG AGAAAGCTTT AAACAAG                                       207
```

(2) INFORMATION FOR SEQ ID NO:7:

(i) SEQUENCE CHARACTERISTICS:
        (A) LENGTH: 219 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA construct"

(xi) SEQUENCE DESCRIPTION: SEQ ID NO:7:

```
ATGAAACCAG TATCTCTGTC TTATCGTTGT CCATGCCGAT TCTTCGAAAG CCATGTTGCC     60

AGAGCCAACG TCAAGCATCT CAAAATTCTC AACACTCCAA ACTGTGCCCT TCAGATTGTA    120

GCCCGGCTGA AGAACAACAA CAGACAAGTG TGCATTGACC CGAAGCTAAA GTGGATTCAG    180

GAGTACCTGG AGAAAGCTTT AAACAAGCGT TTCAAAATG                          219
```

(2) INFORMATION FOR SEQ ID NO:8:

(i) SEQUENCE CHARACTERISTICS:
        (A) LENGTH: 270 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA construct"

(xi) SEQUENCE DESCRIPTION: SEQ ID NO:8:

```
ATGGCAGCTA AAGACGTAAA ACATCACCAT CACCATCACG GTTCTGGTTC TGATGACGAT      60

GACAAAAAAC CAGTATCTCT GTCTTATCGT TGTCCATGCC GATTCTTCGA AAGCCATGTT     120

GCCAGAGCCA ACGTCAAGCA TCTCAAAATT CTCAACACTC CAAACTGTGC CCTTCAGATT     180

GTAGCCCGGC TGAAGAACAA CAACAGACAA GTGTGCATTG ACCCGAAGCT AAAGTGGATT     240

CAGGAGTACC TGGAGAAAGC TTTAAACAAG                                      270
```

(2) INFORMATION FOR SEQ ID NO:9:

(i) SEQUENCE CHARACTERISTICS:
        (A) LENGTH: 282 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA construct"

(xi) SEQUENCE DESCRIPTION: SEQ ID NO:9:

```
ATGGCAGCTA AAGACGTAAA ACATCACCAT CACCATCACG GTTCTGGTTC TGATGACGAT      60

GACAAAAAAC CAGTATCTCT GTCTTATCGT TGTCCATGCC GATTCTTCGA AAGCCATGTT     120

GCCAGAGCCA ACGTCAAGCA TCTCAAAATT CTCAACACTC CAAACTGTGC CCTTCAGATT     180

GTAGCCCGGC TGAAGAACAA CAACAGACAA GTGTGCATTG ACCCGAAGCT AAAGTGGATT     240

CAGGAGTACC TGGAGAAAGC TTTAAACAAG CGTTTCAAAA TG                        282
```

(2) INFORMATION FOR SEQ ID NO:10:

(i) SEQUENCE CHARACTERISTICS:
        (A) LENGTH: 69 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

```
Met Lys Pro Val Ser Leu Ser Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Leu Glu
    50                  55                  60

Lys Ala Leu Asn Lys
65
```

(2) INFORMATION FOR SEQ ID NO:11:

(i) SEQUENCE CHARACTERISTICS:
        (A) LENGTH: 73 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

```
Met Lys Pro Val Ser Leu Ser Tyr Arg Cys Pro Cys Arg Phe Phe Glu
1               5                   10                  15
```

-continued

```
Ser His Val Ala Arg Ala Asn Val Lys His Leu Lys Ile Leu Asn Thr
         20                  25                  30

Pro Asn Cys Ala Leu Gln Ile Val Ala Arg Leu Lys Asn Asn Asn Arg
             35                  40                  45

Gln Val Cys Ile Asp Pro Lys Leu Lys Trp Ile Gln Glu Tyr Leu Glu
 50                  55                  60

Lys Ala Leu Asn Lys Arg Phe Lys Met
 65                  70
```

(2) INFORMATION FOR SEQ ID NO:12:

(i) SEQUENCE CHARACTERISTICS:
        (A) LENGTH: 90 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

```
Met Ala Ala Lys Asp Val Lys His His His His His Gly Ser Gly
 1               5                  10                  15

Ser Asp Asp Asp Lys Lys Pro Val Ser Leu Ser Tyr Arg Cys Pro
             20                  25                  30

Cys Arg Phe Phe Glu Ser His Val Ala Arg Ala Asn Val Lys His Leu
         35                  40                  45

Lys Ile Leu Asn Thr Pro Asn Cys Ala Leu Gln Ile Val Ala Arg Leu
 50                  55                  60

Lys Asn Asn Asn Arg Gln Val Cys Ile Asp Pro Lys Leu Lys Trp Ile
 65                  70                  75                  80

Gln Glu Tyr Leu Glu Lys Ala Leu Asn Lys
             85                  90
```

(2) INFORMATION FOR SEQ ID NO:13:

(i) SEQUENCE CHARACTERISTICS:
        (A) LENGTH: 94 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

```
Met Ala Ala Lys Asp Val Lys His His His His His Gly Ser Gly
 1               5                  10                  15

Ser Asp Asp Asp Lys Lys Pro Val Ser Leu Ser Tyr Arg Cys Pro
             20                  25                  30

Cys Arg Phe Phe Glu Ser His Val Ala Arg Ala Asn Val Lys His Leu
         35                  40                  45

Lys Ile Leu Asn Thr Pro Asn Cys Ala Leu Gln Ile Val Ala Arg Leu
 50                  55                  60

Lys Asn Asn Asn Arg Gln Val Cys Ile Asp Pro Lys Leu Lys Trp Ile
 65                  70                  75                  80

Gln Glu Tyr Leu Glu Lys Ala Leu Asn Lys Arg Phe Lys Met
             85                  90
```

(2) INFORMATION FOR SEQ ID NO:14:

(i) SEQUENCE CHARACTERISTICS:
        (A) LENGTH: 68 amino acids

```
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:14:

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
                35                  40                  45

Val Cys Ile Asp Pro Lys Leu Lys Trp Ile Gln Glu Tyr Leu Glu Lys
        50                  55                  60

Ala Leu Asn Lys
65

(2) INFORMATION FOR SEQ ID NO:15:

(i) SEQUENCE CHARACTERISTICS:
      (A) LENGTH: 72 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:15:

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
                35                  40                  45

Val Cys Ile Asp Pro Lys Leu Lys Trp Ile Gln Glu Tyr Leu Glu Lys
        50                  55                  60

Ala Leu Asn Lys Arg Phe Lys Met
65              70
```

CHEMOKINE WITH AMINO-TERMINAL MODIFICATIONS

This application claims benefit of Ser. No. 60/113,672, converted from Ser. No.08/955,826, filed Oct. 22, 1997, which is a continuation-in-part of Ser. No. 08/808,720, filed Feb. 28, 1997, now U.S. Pat. No. 6,100,387.

BACKGROUND OF THE INVENTION

The present invention relates generally to amino-terminal-modified (N-terminal-modified) chemokines and the use of such chemokines to inhibit the interaction between chemokine receptors and naturally occurring ligands of those receptors. More specifically, the invention relates to the expression in host cells of recombinant polynucleotide sequences encoding chemokines having additional amino acids or other chemical groups attached to their amino termini, and the use of such N-terminal-modified chemokines as research tools for identifying chemokine receptors, as vaccine adjuvants, as agents for the chemotactic recruitment of migratory cells, as agents for the stimulation or inhibition of angiogenesis, as agents against autoimmune diseases and inflammation, and as agents to inhibit the binding of HIV to certain receptors and the infection of susceptible cells by HIV.

Chemokines (or chemotactic cytokines) are a class of cytokine molecules capable of chemotactically attracting migratory cells, and are involved in cell recruitment and activation in inflammation. Chemokines generally have small molecular weights in the range of 8–10 kDa and, like other small proteins such as cytokines, are believed to be rapidly inactivated in vivo, resulting in relatively short biological half-lives for these proteins. Most chemokines can be divided into two subgroups, CXC (alpha chemokines) or CC (beta chemokines), on the basis of the spacing of two highly-conserved cysteine amino acids near the amino terminus of these proteins. Within the CXC and CC subgroups, chemokines are further grouped into related families based on amino acid sequence similarity between them. CXC chemokine families include the IP-10 and Mig family; the GROα, GROβ, and GROγ family; the interleukin-8 (IL-8) family; and the platelet factor 4 (PF4) family; other CXC chemokines that have been identified are: C10, DC-CK1, CKα1, CKα2, ENA-78, GCP-2, and platelet basic protein (PBP) and its derivatives CTAPIII, β-thromboglobulin, and NAP-2. CC chemokine families include the monocyte chemoattractant protein (MCP) family including MCP-1 to MCP-4; the family including macrophage inhibitory protein-1α (MIP-1α), macrophage inhibitory protein-1β (MIP-1β), and regulated on activation normal T cell expressed (RANTES) protein; and the lymphotactin family; other CC chemokines that have been identified are: ATAC, eotaxin, eotaxin2, I-309, HCC-1, HCC-2, HCC-3, LARC/MIP-3α, MIP-3β, PARC, TARC, 6Ckine, ELC, SLC, CKβ4, CKβ6, CKβ7, CKβ8, CKβ9, CKβ11, CKβ12, CKβ13. $CX_3C$ (or CX3C) is a recently identified member of a new class of chemokines. The chemokines stromal cell-derived factor 1α (SDF-1α) and stromal cell-derived factor 1β (SDF-1β) form a chemokine family that is approximately equally related by amino acid sequence similarity to the CXC and CC chemokine subgroups. Individual members of the chemokine families are known to be bound by at least one chemokine receptor, with CXC chemokines generally bound by members of the CXCR class of receptors (CXCR1 –CXCR4), and CC chemokines by members of the CCR class of receptors (CCR1 –CCR8). For example, SDF-1α is known to be a ligand for the CXCR receptor fusin/CXCR4, and MIP-1α is bound by the CCR receptors CCR1, CCR4, and CCR5. Other chemokine receptors that have been identified are: BLR1, MDR15, EBI-1, CMKBRL1, HCMV-US28, HSV-ECRF3, and Duffy antigen (DARC).

The presence of a chemokine gradient attracts migratory cells such as lymphocytes, leukocytes, and antigen-presenting cells (APCs) that may participate in autoimmune reactions, inflammation, or normal immune responses, or that may release other intercellular factors to stimulate or inhibit angiogenesis, bone resorption, or other cellular processes. For example, the initiation of autoimmune disease requires the infiltration or recruitment of lymphocytes able to respond against self proteins into the organ bearing the antigenic self proteins. Inflammatory atherosclerotic lesions are due in part to infiltration of the vascular compartment by leukocytes recruited to the site. To induce an immune response, antigenic proteins and glycoproteins must bind to the surface of B lymphocytes to stimulate antibody production, and must be taken up by antigen-presenting cells, processed, and represented to T lymphocytes to mediate a T-lymphocyte response. Migratory cells that secrete IP-10 or IL-8, when attracted by a chemokine gradient to a particular site, respectively may inhibit or stimulate the formation of blood vessels at that site. Chemokines may be used to establish a chemoattractive gradient for migratory cells that are expressing the appropriate chemokine receptors, or to obscure an existing chemoattractive gradient.

Chemokine receptors are also involved in functions other than chemotaxis, such as interacting with viral proteins. HIV-1 is known to bind to certain proteins on the surface of cells in order to gain entrance into these cells and replicate or integrate the viral gene into the host DNA. The CD4 protein on T lymphocytes and other cells, including certain antigen presenting cells, has been shown to be bound by the HIV-1 viral envelope protein gp120. This is believed to induce in gp120 a conformational change that then exposes regions of gp120 and perhaps CD4 that subsequently bind to a chemokine receptor. To date CXCR4 (also known as fusin), CCR5, and several other chemokine receptors have been identified as co-receptors for HIV-1. Monocyte-tropic (M-tropic) isolates of HIV-1 require interaction with CCR5 in order to infect cells, while T-lymphocyte-tropic (T-tropic) HIV-1 isolates require another coreceptor, CXCR4, for infection. There is some evidence indicating that HIV-1 can also use other CCR receptors such as CCR2 and CCR3 to gain entry into cells. For some HIV-2 isolates, it appears that certain chemokine receptors such as fusin/CXCR4 alone can provide the cell-surface protein needed for binding and entrance into the cell.

There is a continuing requirement for new compositions that will enhance, alter, or inhibit chemokine-receptor interactions, and for methods for their use.

SUMMARY OF THE INVENTION

Applicants have for the first time constructed novel polynucleotides encoding certain amino-terminal-modified chemokines comprising chemokines or polypeptides derived from chemokines. Amino-terminal-modified chemokines expressed from these constructs have exhibited novel and unexpected properties, including novel interactions with cells expressing chemokine receptors.

In one embodiment, the present invention provides a composition comprising an isolated polynucleotide encoding an amino-terminal-modified chemokine, wherein the chemokine is selected from the group consisting of SDF-1α, SDF-1β, IP-10, Mig, GROα, GROβ, GROγ, interleukin-8, PF4, ENA-78, GCP-2, PBP, CTAP-III, β-thromboglobulin, NAP-2, C10, DC-CK1, CKα1, CKα2, MCP-1, MCP-2, MCP-3, MCP-4, MIP-1α, MIP-1β, lymphotactin, ATAC, eotaxin, eotaxin2, I-309, HCC-1, HCC-2, HCC-3, LARC/ MIP-3α, MIP-3β, PARC, TARC, 6Ckine, ELC, SLC, CKβ4, CKβ6, CKβ7, CKβ8, CKβ9, CKβ11, CKβ12, CKβ13, and CX3C. Preferably, the amino-terminal-modified chemokine comprises at least one methionine residue covalently attached to the amino terminus of the chemokine, or at least one aminooxypentane residue covalently attached to the amino terminus of the chemokine, or at least one GroHEK peptide covalently attached to the amino terminus of the chemokine. In certain preferred embodiments, the polynucleotide is operably linked to an expression control sequence, or is further operably linked to a sequence directing secretion of the expressed amino-terminal-modified chemokine. The invention also provides a host cell, preferably a mammalian cell, transformed with such polynucleotide compositions.

Processes are also provided for producing an amino-terminal-modified chemokine, which comprise:

(a) growing a culture of the host cell transformed with such polynucleotide compositions in a suitable culture medium; and (b) purifying the amino-terminal-modified chemokine from the culture.

The polypeptide produced according to such methods is also provided by the present invention.

Processes are also provided for producing an amino-terminal-modified chemokine in a host, which comprise:

(a) isolating stem cells from the host;

(b) transforming the stem cells with such polynucleotide compositions; and (c) reintroducing the transformed stem cells into the host, wherein the transformed stem cells will express the amino-terminal-modified chemokine.

Another embodiment provides a composition comprising an isolated polynucleotide encoding an amino-terminal-modified chemokine, wherein the amino-terminal-modified chemokine is derived from a chemokine selected from the group consisting of SDF-1α, SDF-1β, IP-10, Mig, GROα, GROβ, GROγ, interleukin-8, PF4, ENA-78, GCP-2, PBP, CTAP-III, β-thromboglobulin, NAP-2, C10, DC-CK1, CKα1, CKα2, MCP-1, MCP-2, MCP-3, MCP4, MIP-1α, MIP-1β, RANTES, lymphotactin, ATAC, eotaxin, eotaxin2, I-309, HCC-1, HCC-2, HCC-3, LARC/MIP-3α, MIP-3β, PARC, TARC, 6Ckine, ELC, SLC, CKβ4, CKβ6, CKβ7, CKβ8, CKβ9, CKβ11, CKβ12, CKβ13, and CX3C.

In another embodiment, the present invention provides a composition comprising an isolated polynucleotide encoding an amino-terminal-modified chemokine, wherein the polynucleotide is selected from the group consisting of:

(a) a polynucleotide comprising the nucleotide sequence of SEQ ID NO:6;

(b) a polynucleotide comprising the nucleotide sequence of the protein-coding sequence of the polynucleotide encoding met-hSDF-1α deposited under accession number ATCC 98506;

(c) a polynucleotide encoding an amino-terminal-modified chemokine comprising the amino acid sequence of SEQ ID NO:10;

(d) a polynucleotide encoding a protein comprising an amino-terminal fragment of the amino acid sequence of SEQ ID NO:10;

(e) a polynucleotide comprising a nucleotide sequence complementary to any one of the polynucleotides specified in (a)–(d) above; and (f) a polynucleotide capable of hybridizing under stringent conditions to any one of the polynucleotides specified in (a)–(e) above.

In a further embodiment, the present invention provides a composition comprising an isolated polynucleotide encoding an amino-terminal-modified chemokine, wherein the polynucleotide is selected from the group consisting of:

(a) a polynucleotide comprising the nucleotide sequence of SEQ ID NO:7;

(b) a polynucleotide comprising the nucleotide sequence of the protein-coding sequence of the polynucleotide encoding met-hSDF-1β deposited under accession number ATCC 98507;

(c) a polynucleotide encoding an amino-terminal-modified chemokine comprising the amino acid sequence of SEQ ID NO:11;

(d) a polynucleotide encoding a protein comprising an amino-terminal fragment of the of the amino acid sequence of SEQ ID NO:11;

(e) a polynucleotide comprising a nucleotide sequence complementary to any one of the polynucleotides specified in (a)–(d) above; and (f) a polynucleotide capable of hybridizing under stringent conditions to any one of the polynucleotides specified in (a)–(e) above.

In another embodiment, the present invention provides a composition comprising an isolated polynucleotide encoding an amino-terminal-modified chemokine, wherein the polynucleotide is selected from the group consisting of:

(a) a polynucleotide comprising the nucleotide sequence of SEQ ID NO:8;

(b) a polynucleotide comprising the nucleotide sequence of the protein-coding sequence of the polynucleotide encoding GroHEK/hSDF-1α deposited under accession number ATCC 98508;

(c) a polynucleotide encoding an amino-terminal-modified chemokine comprising the amino acid sequence of SEQ ID NO:12;

(d) a polynucleotide encoding a protein comprising an amino-terminal fragment of the of the amino acid sequence of SEQ ID NO:12;

e) a polynucleotide comprising a nucleotide sequence complementary to any one of the polynucleotides specified in (a)–(d) above; and (f) a polynucleotide capable of hybridizing under stringent conditions to any one of the polynucleotides specified in (a)–(e) above.

In a further embodiment, the present invention provides a composition comprising an isolated polynucleotide encoding an amino-terminal-modified chemokine, wherein the polynucleotide is selected from the group consisting of:

(a) a polynucleotide comprising the nucleotide sequence of SEQ ID NO:9;

(b) a polynucleotide comprising the nucleotide sequence of the protein-coding sequence of the polynucleotide encoding GroHEK/hSDF-1β deposited under accession number ATCC 98509;

(c) a polynucleotide encoding an amino-terminal-modified chemokine comprising the amino acid sequence of SEQ ID NO:13;

(d) a polynucleotide encoding a protein comprising an amino-terminal fragment of the of the amino acid sequence of SEQ ID NO:13;

(e) a polynucleotide comprising a nucleotide sequence complementary to any one of the polynucleotides specified in (a)–(d) above; and (f) a polynucleotide capable of hybridizing under stringent conditions to any one of the polynucleotides specified in (a)–(e) above.

In a further embodiment, the present invention provides a composition comprising an isolated polynucleotide encoding an amino-terminal-modified chemokine, wherein the chemokine binds the fusin/CXCR4 chemokine receptor.

The present invention also provides a composition comprising an isolated polynucleotide encoding an amino-terminal-modified chemokine, wherein the amino-terminal-modified chemokine is a more effective inhibitor of HIV infection than the corresponding unmodified chemokine.

In other embodiments, the present invention provides a composition comprising an amino-terminal-modified chemokine, wherein the chemokine is selected from the group consisting of SDF-1α, SDF-1β, IP-10, Mig, GROα, GROβ, GROγ, interleukin-8, PF4, ENA-78, GCP-2, PBP, CTAP-III, β-thromboglobulin, NAP-2, C10, DC-CK1, CKα1, CKα2, MCP-1, MCP-2, MCP-3, MCP4, MIP-1α, MIP-1β, lymphotactin, ATAC, eotaxin, eotaxin2, I-309, HCC-1, HCC-2, HCC-3, LARC/MIP-3α, MIP-3β, PARC, TARC, 6Ckine, ELC, SLC, CKβ4, CKβ6, CKβ7, CKβ8, CKβ9, CKβ11, CKβ12, CKβ13, and CX3C. Preferably, the amino-terminal-modified chemokine comprises at least one methionine residue covalently attached to the amino terminus of the chemokine, or at least one aminooxypentane residue covalently attached to the amino terminus of the chemokine, or at least one GroHEK peptide covalently attached to the amino terminus of the chemokine.

Another embodiment provides a composition comprising an amino-terminal-modified chemokine, wherein the amino-terminal-modified chemokine is derived from a chemokine selected from the group consisting of SDF-1α, SDF-1β, IP-10, Mig, GROα, GROβ, GROγ, interleukin-8, PF4, ENA-78, GCP-2, PBP, CTAP-III, β-thromboglobulin, NAP-2, C10, DC-CK1, CKα1, CKα2, MCP-1, MCP-2, MCP-3, MCP4, MIP-1α, MIP-1β, RANTES, lymphotactin, ATAC, eotaxin, eotaxin2, I-309, HCC-1, HCC-2, HCC-3, LARC/MIP-3α, MIP-3β, PARC, TARC, 6Ckine, ELC, SLC, CKβ4, CKβ6, CKβ7, CKβ8, CKβ9, CKβ11, CKβ12, CKβ13, and CX3C.

In another embodiment, the present invention provides a composition comprising an amino-terminal-modified chemokine wherein the amino-terminal-modified chemokine comprises an amino acid sequence selected from the group consisting of:

(a) the amino acid sequence of SEQ ID NO:10;

(b) the amino acid sequence of the protein encoded by the met-hSDF-1α polynucleotide deposited under accession number ATCC 98506;

(c) amino-terminal fragments of the amino acid sequence of SEQ ID NO:10; and (d) amino-terminal fragments of the amino acid sequence of the protein encoded by the met-hSDF-1α polynucleotide deposited under accession number ATCC 98506.

In a further embodiment, the present invention provides a composition comprising an amino-terminal-modified chemokine wherein the amino-terminal-modified chemokine comprises an amino acid sequence selected from the group consisting of:

(a) the amino acid sequence of SEQ ID NO:11;

(b) the amino acid sequence of the protein encoded by the met-hSDF-1β polynucleotide deposited under accession number ATCC 98507;

(c) amino-terminal fragments of the amino acid sequence of SEQ ID NO:11; and (d) amino-terminal fragments of the amino acid sequence of the protein encoded by the met-hSDF-1β polynucleotide deposited under accession number ATCC 98507.

In another embodiment, the present invention provides a composition comprising an amino-terminal-modified chemokine wherein the amino-terminal-modified chemokine comprises an amino acid sequence selected from the group consisting of:

(a) the amino acid sequence of SEQ ID NO:12;

(b) the amino acid sequence of the protein encoded by the GroHEK/hSDF-1α polynucleotide deposited under accession number ATCC 98508;

(c) amino-terminal fragments of the amino acid sequence of SEQ ID NO:12; and (d) amino-terminal fragments of the amino acid sequence of the protein encoded by the GroHEK/hSDF-1α polynucleotide deposited under accession number ATCC 98508.

In a further embodiment, the present invention provides a composition comprising an amino-terminal-modified chemokine wherein the amino-terminal-modified chemokine comprises an amino acid sequence selected from the group consisting of:

(a) the amino acid sequence of SEQ ID NO:13;

(b) the amino acid sequence of the protein encoded by the GroHEK/hSDF-1β polynucleotide deposited under accession number ATCC 98509;

(c) amino-terminal fragments of the amino acid sequence of SEQ ID NO:13; and (d) amino-terminal fragments of the amino acid sequence of the protein encoded by the GroHEK/hSDF-1β polynucleotide deposited under accession number ATCC 98509.

Compositions comprising amino-terminal-modified chemokines of the present invention may further comprise a pharmaceutically acceptable carrier. Compositions comprising an antibody which reacts with an amino-terminal-modified chemokine but does not react with the unmodified chemokine are also provided by the present invention.

The present invention also provides methods for identifying molecules capable of interacting with an amino-terminal-modified chemokine which comprise:

(a) combining a composition comprising an amino-terminal-modified chemokine with an indicator molecule and with a composition comprising molecules to be tested for interaction; and (b) detecting the presence of altered indicator molecules.

Methods are also provided for altering receptor function which comprise causing a receptor to bind at least one amino-terminal-modified chemokine.

The present invention also provides methods for inhibiting the interaction between a chemokine receptor and a ligand of the receptor which comprise causing the receptor to bind at least one amino-terminal-modified chemokine.

Methods are also provided for decreasing receptor function which comprise causing a receptor to bind at least one amino-terminal-modified chemokine, resulting in a decrease in the number of functional receptor molecules.

The present invention also provides methods for preventing, treating, or ameliorating HIV infection which comprise administering therapeutically effective amounts of at least one composition comprising an amino-terminal-modified chemokine.

Preferably, the compositions administered comprise:
(a) an amino-terminal-modified chemokine comprising a chemokine selected from the group consisting of SDF-1α and SDF-1β; and
(b) an amino-terminal-modified chemokine comprising a chemokine selected from the group consisting of MIP-1α and MIP-1β.

Methods are additionally provided for identifying amino-terminal-modified chemokines capable of inhibiting the interaction of HIV with an HIV receptor which comprise:
(a) combining a composition comprising an amino-terminal-modified chemokine with a composition comprising HIV receptor molecules, forming a first mixture;
(b) combining the first mixture with a composition comprising HIV molecules, forming a second mixture;
(c) combining a composition comprising HIV receptor molecules with a composition comprising HIV molecules, forming a control mixture;
(d) determining the amount of interaction between the HIV molecules and the HIV receptor molecules in the second mixture and in the control mixture; and
(e) comparing the amount of interaction between the HIV molecules and the HIV receptor molecules in the second mixture with the amount of interaction between the HIV molecules and the HIV receptor molecules in the control mixture, wherein the amino-terminal-modified chemokine inhibits the interaction of HIV with the HIV receptor when the amount of interaction between the HIV molecules and the HIV receptor molecules is less in the second mixture than in the control mixture.

The present invention also provides methods for identifying amino-terminal-modified chemokines capable of inhibiting the infection by HIV of cells susceptible to HIV infection which comprise:
(a) combining a composition comprising an amino-terminal-modified chemokine with a composition comprising cells susceptible to HIV infection, forming a first mixture;
(b) combining the first mixture with a composition comprising HIV particles, forming a second mixture;
(c) combining a composition comprising cells susceptible to HIV infection with a composition comprising HIV particles, forming a control mixture;
(d) determining the amount of infection of the susceptible cells by HIV in the second mixture and in the control mixture; and
(e) comparing the amount of infection of the susceptible cells by HIV in the second mixture with the amount of infection of the susceptible cells by HIV in the control mixture, wherein the amino-terminal-modified chemokine inhibits the infection of the susceptible cells by HIV when the amount of infection of the susceptible cells by HIV is less in the second mixture than in the control mixture.

The present invention also provides methods for attracting migratory cells to a region of an organism which comprise administering therapeutically effective amounts of at least one composition comprising an amino-terminal-modified chemokine.

Methods are also provided for stimulating angiogenesis which comprise administering therapeutically effective amounts of at least one composition comprising an amino-terminal-modified chemokine.

The present invention additionally provides methods for inhibiting angiogenesis which comprise administering therapeutically effective amounts of at least one composition comprising an amino-terminal-modified chemokine.

Methods are also provided for preventing, treating, or ameliorating an inflammatory condition which comprise administering therapeutically effective amounts of at least one composition of comprising an amino-terminal-modified chemokine.

Additionally, the present invention provides methods for preventing, treating, or ameliorating an autoimmune condition which comprise administering therapeutically effective amounts of at least one composition comprising an amino-terminal-modified chemokine.

Methods are also provided for inducing an immune response which comprise administering a vaccine and therapeutically effective amounts of at least one composition comprising an amino-terminal-modified chemokine.

The present invention also provides a composition comprising an amino-terminal-modified chemokine, wherein the chemokine binds the fusin/CXCR4 chemokine receptor.

In a further embodiment, the present invention provides a composition comprising an amino-terminal-modified chemokine, wherein the amino-terminal-modified chemokine is a more effective inhibitor of HIV infection than the corresponding unmodified chemokine.

Additionally, methods are provided for preventing, treating, or ameliorating HIV infection of a host which comprises:
(a) isolating stem cells from the host;
(b) transforming the stem cells with at least one composition comprising a polynucleotide of the present invention; and
(c) reintroducing the transformed stem cells into the host, wherein the transformed stem cells will express at least one amino-terminal-modified chemokine.

Preferably, the transformed stem cells express an amino-terminal-modified chemokine comprising a chemokine selected from the group consisting of SDF-1α and SDF-1β; and an amino-terminal-modified chemokine comprising a chemokine selected from the group consisting of MIP-1α and MIP-1β.

Other aspects and advantages of the present invention will be apparent upon consideration of the following detailed description of preferred embodiments thereof.

DETAILED DESCRIPTION OF THE INVENTION

Figure 1:
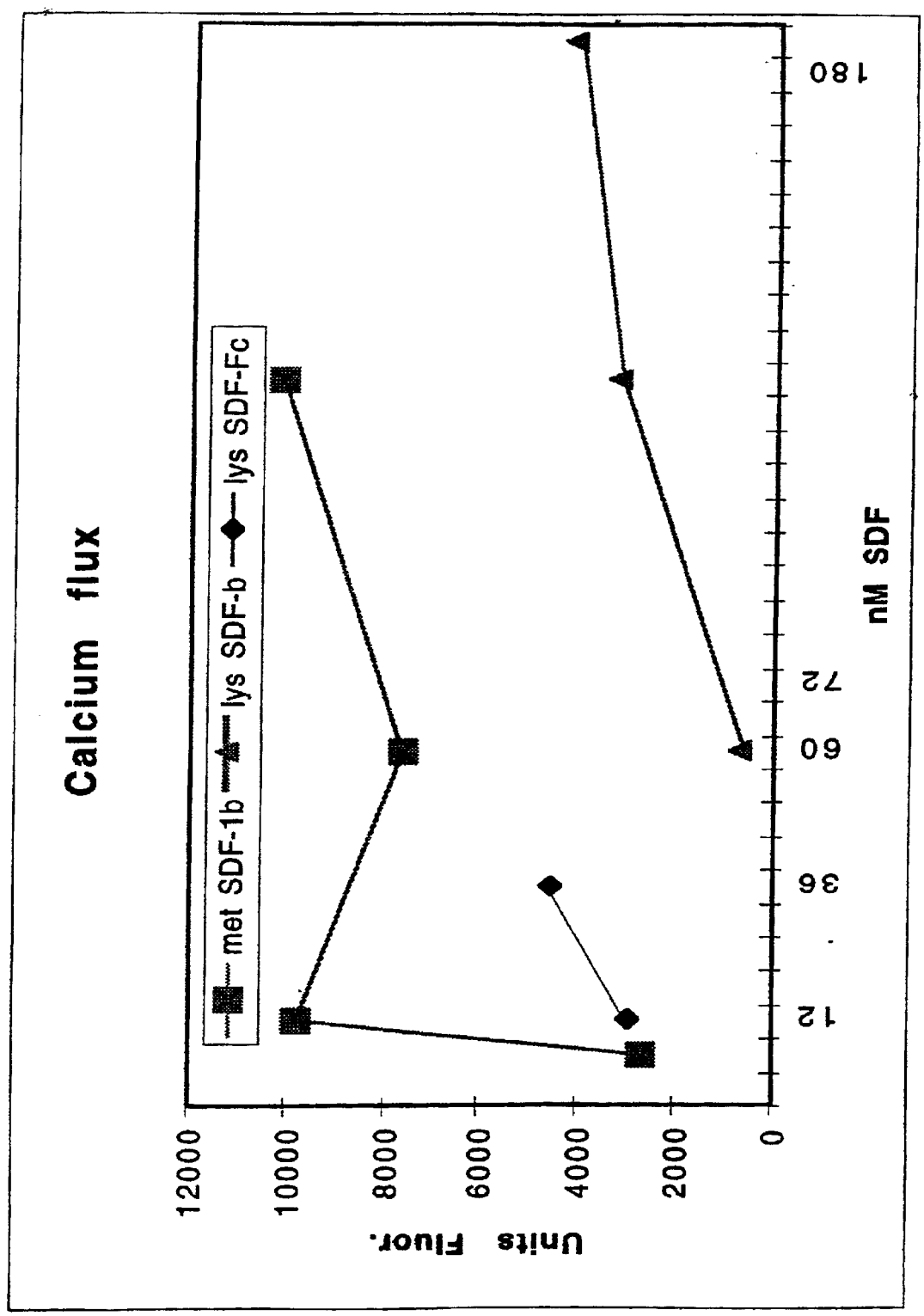
FIG. 1 is a graphical representation of the influx of calcium into cells produced by the binding of N-terminal-modified or unmodified chemokines to chemokine receptors, as described in Example 2.

The present inventors have for the first time constructed polynucleotides expressing novel amino-terminal-modified chemokines. These N-terminal modified chemokines interact with chemokine receptors and have novel and unexpected properties.

As used herein, "chemokine" includes all protein molecules with chemotactic activity. An amino-terminal-modified chemokine is "derived from a chemokine" when the chemokine that has been modified at its amino terminus has itself been derived from a chemokine by any kind of alteration, addition, insertion, deletion, mutation, substitution, replacement, or other modification. Chemotactic activity for a particular cell population is the direct or indirect stimulation of the directed orientation or movement of such cell population. Preferably, the cell population comprises circulating blood cells and/or bone marrow stem cells. More preferably, the cell population may include monocytes, B cells, T cells, basophils, eosinophils, neutrophils, natural killer (NK) cells, and bone marrow stem cells. Most preferably, the cell population may include monocytes, T cells, basophils, and bone marrow stem cells. Preferably, the chemokine has the ability to directly stimulate directed movement of cells. Whether a particular polypeptide has chemotactic activity for a population of cells can be readily determined by employing the polypeptide in any known assay for cell chemotaxis. Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed. by J. E. Coligan, A. M. Kruisbeek, D. H. Margulies, E. M. Shevach, W. Strober, Pub. by Greene Publishing Associates and Wiley-Interscience (Chapter 6.12, Measurement of alpha and beta Chemokines 6.12.1–6.12.28); Taub et al., J. Clin. Invest. 95:1370–1376, 1995; Lind et al., APMIS 103:140–146, 1995; Muller et al:, Eur. J. Immunol. 25: 1744–1748; Gruber et al., J. of Immunol. 152:5860–5867, 1994; Johnston et al., J. of Immunol. 153: 1762–1768, 1994; all of which are incorporated herein by reference.

As used herein, "covalently attached" means the attachment of molecules to each other by covalent chemical bonds, either directly or through a linker molecule that is itself covalently attached to said molecules.

As used herein, "amino-terminal-modified chemokine" includes the result of covalently attaching any chemical moiety to the N-terminus of a chemokine polypeptide, wherein the chemical moiety may include any amino acid(s) or chemically modified amino acid(s); fragments of or entire chemokines, cytokines, immunoglobulins, antigens, kinases, proteases (including without limitation CD26, HIV proteases, granzymes, or cathepsin G), other enzymes, or structural proteins; polypeptides derived from the foregoing by any form of alteration, addition, insertion, deletion, mutation, substitution, replacement, or other modification, including without limitation alterations to the Leu-25 residue of the mature IL-8 polypeptide (Wells et al., 1996, *J. Leukoc. Biol.* 59: 53–60), alterations to the corresponding leucine residue of SDF-1α and SDF-1β (e.g. residue 47 of SEQ ID NO:s 1 and 2, residue 27 of SEQ ID NO:s 10 and 11, residue 48 of SEQ ID NO:s 12 and 13, and residue 26 of SEQ ID NO:s 14 and 15), and alterations to the tyrosine-28 residue of mature MIP-1α and MIP-1β (Wells et al., 1996, *J. Leukoc. Biol.* 59: 53–60); antibody-binding tags such as His, Flag, or myc; lectin-binding domains; toxins; etc. Preferably, the chemical moiety attached to the N-terminus of the chemokine polypeptide does not interfere with binding of the chemokine polypeptide to its receptor(s). More preferably, the amino-terminal-modified chemokine comprises a methionine residue covalently attached to the amino-terminus of the naturally-occuring mature (or secreted) form(s) of the chemokine. In another more preferred embodiment, a serine or threonine residue is attached to the N-terminus of the chemokine (if its N-terminal residue is not already serine or threonine), and the chemokine is then subjected to a mild periodate oxidation to convert the serine or threonine into an aldehyde, followed by reaction with aminooxypentane (AOP) to form the desired AOP-chemokine oxime (see Simmons et al., 1997, *Science* 276: 276–279, incorporated herein by reference). Other methods for preparing amino-terminal-modified chemokines are described in U.S. Pat. No. 5,656,456, incorporated herein by reference. In another preferred embodiment, the chemical moiety attached to the N-terminus of the chemokine polypeptide comprises a enzymatic or chemical cleavage site so that the amino-terminal-modified chemokine may be cleaved to produce a molecule or molecule(s) having a desired activity. More preferably, a GroHEK peptide (SEQ ID NO:5) comprising an enterokinase target amino acid sequence is attached to the N-terminus of a chemokine, optionally with additional amino acids(s) linking the Gro-HEK peptide to the chemokine. The GroHEK peptide can be left attached to the chemokine as an N-terminal modification, or it can be cleaved off by enterokinase so that the additional linking amino acid(s) are now the N-terminal additions to the chemokine. Also more preferably, a peptide comprising an HIV protease target amino acid sequence is attached to the N-terminus of a chemokine to form an HIV protease cleavage site, optionally with additional amino acids(s) linking the HIV protease recognition peptide to the chemokine. The HIV protease recognition peptide can be left attached to the chemokine as an N-terminal modification, or it can be cleaved off by the HIV protease so that the additional linking amino acid(s), if any, are now the N-terminal additions to the chemokine. Examples of amino acid sequences cleaved by HIV proteases are described in Tomasselli and Heinrikson, *Methods in Enzymology* 241: 279–301, 1994, incorporated herein by reference. In another preferred embodiment, the chemical moiety attached to the N-terminus of the chemokine polypeptide comprises a molecule with a desired activity, so that the N-terminal-modified chemokine also possesses this desired activity. More preferably, the chemical moiety attached to the N-terminus of the chemokine polypeptide comprises a protease.

Fragments of amino-terminal-modified chemokines are also encompassed by the present invention. Preferably, such fragments retain the desired activity of the amino-terminal-modified chemokine or modify it to create a desired activity. Fragments of amino-terminal-modified chemokines may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. The amino-terminal-modified chemokines provided herein also include polypeptides characterized by amino acid sequences similar to those of purified proteins but into which modifications are naturally provided or deliberately engineered. For example, modifications in the polypeptide or DNA sequences can be made by those skilled in the art using known techniques. Modifications of interest in the polypeptide sequences may include the alteration, addition, insertion, deletion, mutation, substitution, replacement, or other modification of a selected amino acid residue in the coding sequence. As one example, one or more of the cysteine residues may be deleted or replaced with another amino acid to alter the conformation of the molecule. Also, the amino acid sequence of the polypeptide may be altered using random mutation techniques. It is also possible to attach to polypeptides other moieties, including without limitation carbohydrates, lipids, or polyethylene glycol, or to remove or alter such moieties. Techniques for such alterations, additions, insertions, deletions, mutations, substitutions, replacements, or other modifications are well known to those skilled in the art (see, e.g., U.S. Pat. No. 4,518,584). Preferably, such alteration, addition, insertion, deletion, mutation, substitution, replacement, or other modification retains the desired activity of the amino-terminal-modified chemokine or modifies it to create a desired activity.

Other fragments and derivatives of the sequences of amino-terminal-modified chemokines which would be expected to retain biological activity and may thus be useful for screening or other immunological methodologies may also be easily made by those skilled in the art given the disclosures herein. Such modifications are believed to be encompassed by the present invention. For example, amino-terminal-modified chemokines can be attached through "linker" sequences to the Fc portion of an immunoglobulin. For a bivalent form of the amino-terminal-modified chemokine, such a fusion could be to the Fc portion of an IgG molecule. Other immunoglobulin isotypes may also be used to generate such fusions. For example, an amino-terminal-modified chemokine-IgM fusion would generate a decavalent form of the chemokine. In addition, it is possible to create a multivalent form of an amino-terminal-modified chemokine by connecting the amino-terminal-modified chemokine through a $P_i$ linkage to the phosphatidyl inositol present in micellular preparations.

The present invention also provides both amino-terminal-modified chemokines and forms of amino-terminal-modified chemokines that further include secretory leader sequences. When an amino-terminal-modified chemokine to which a secretory leader sequence has been attached is expressed in host cells, the secretory leader sequence is cleaved off as the amino-terminal-modified chemokine is translated, producing a secreted amino-terminal-modified chemokine that has the desired amino-terminal modification, or has a precursor molecule attached to the N-terminus of the chemokine that may be converted to the desired N-terminal-modification by a chemical or biological process. The secretory leader sequence may be the same as that found on the naturally-occurring full-length form of the chemokine, or it may be a "synthetic" secretory leader sequence specifically chosen for expression of the amino-terminal modified chemokine in a particular host cell.

Amino-terminal-modified chemokines including those comprising chemokines that are species homologs of disclosed chemokines are also provided by the present invention. Species homologs may be isolated and identified by making suitable probes or primers from the sequences provided herein and screening a suitable nucleic acid source from the desired species. The invention also encompasses allelic variants of the disclosed chemokines or chemokine-encoding polynucleotides; that is, naturally-occurring alternative forms of the disclosed polynucleotides which also encode polypeptides which are identical, homologous, or related to that encoded by the polynucleotides.

The present invention also includes polynucleotides capable of hybridizing under stringent conditions, preferably highly stringent conditions, to polynucleotides described herein. Highly stringent conditions include, for example, 0.2×SSC at 65° C.; stringent conditions include, for example, 4×SSC at 65° C. or 50% formamide and 4×SSC at 42° C. Preferably, such hybridizing polynucleotides are at least 70% homologous by sequence identity (more preferably, at least 80% homologous; most preferably 90% or 95% homologous) with the polynucleotide of the present invention to which they hybridize.

Expression and Purification of Amino-Terminal-Modified Chemokines

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference. As used herein, an insect cell capable of expressing a polynucleotide of the present invention is "transformed."

The protein of the invention may also be expressed as a product of transgenic animals, e.g., as a component of the milk of transgenic cows, goats, pigs, or sheep which are characterized by somatic or germ cells containing a nucleotide sequence encoding the protein.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLabs (Beverly, Mass.), Pharmacia (Piscataway, N.J.) and InVitrogen (San Diego, Calif.), respectively. The protein can also be tagged with an epitope and subsequently purified by using a specific antibody directed to such epitope. One such epitope ("Flag") is commercially available from Kodak (New Haven, Conn.).

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or imnunoaffinity chromatography.

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein may also be produced by known conventional chemical synthesis. Methods for constructing the proteins of the present invention by synthetic means are known to those skilled in the art. The synthetically-constructed protein sequences, by virtue of sharing primary, secondary, or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

Uses of Amino-Terminal-Modified Chemokines

Amino-terminal-modified chemokines can be used as tools for identifying cells expressing receptor for the chemokine, or for studying binding of chemokine to isolated receptor molecules. The amino-terminal-modified chemokine when incubated with cells expressing a receptor for the chemokine will bind to these cells and can be indicated using an indicator molecule, preferably a commercially available fluorescently tagged antibody or other protein, able to bind to and be localized by the amino-terminal-modified chemokine. This will indicate cells having a surface receptor for a given chemokine as well as the density of this receptor on the cell surface.

Interactions between amino-terminal-modified chemokines and chemokine receptors or other molecules can also be detected directly by measuring changes in surface plasmon resonance using a BIAcore™ sensor (Pharmacia). The chemokine receptor or the amino-terminal-modified chemokine can be covalently immobilized to different flow cells on the BIAcore™ sensor chip as recommended by the manufacturer. Molecules to be tested for interaction are then injected across the flow cells and binding is detected as a change in resonance units, a reflection of the mass of protein bound to the sensor chip surface. In this example the molecules of the flow cells are acting as indicator molecules, as their state is altered when the molecules being tested interact with the chemokine receptor or the amino-terminal-modified chemokine that is covalently immobilized to the flow cells.

Interactions between amino-terminal-modified chemokines and chemokine receptors or other molecules can also be detected using a two-hybrid or "interaction trap" system such as that developed in yeast. (See Bai and Elledge, 1996, *Methods in Enzymology* 273: 331–347; Allen et al., 1995, *Trends in Biochem. Sci.* 20: 511–516; and White, 1996, *Proc. Natl. Acad. Sci. USA* 93: 10001–10003; all of which are incorporated herein by reference.) For example, the amino-terminal-modified chemokine is fused or covalently linked to a protein having a DNA binding domain, and the indicator molecule comprises the molecule to be tested fused or covalently linked to a protein having a transcription activation domain. Interaction between the amino-terminal-modified chemokine and the tested-molecule portion of the indicator molecule allows the transcription activation portion of the indicator molecule to activate transcription of a reporter gene.

Other suitable assays for receptor-chemokine binding activity include without limitation those described in: Current Protocols in Immunology, edited by J. E. Coligan, A. M. Kruisbeek, D. H. Margulies, E. M. Shevach, W. Strober, published by Greene Publishing Associates and Wiley-Interscience (Chapter 7.28, Measurement of Cellular Adhesion under Static Conditions 7.28.1–7.28.22); Takai et al., *Proc. Natl. Acad. Sci. USA* 84:6864–6868, 1987; Bierer et al., *J. Exp. Med.* 168:1145–1156, 1988; Rosenstein et al., *J. Exp. Med.* 169:149–160, 1989; Stoltenborg et al., *J. Immunol. Methods* 175:59–68, 1994; Stitt et al., *Cell* 80:661–670, 1995; Daugherty et al., *J. Exp. Med.* 183: 2349–2354, 1996; Wu et al., *Nature* 384: 179–183, 1996; and Trkola et al., *Nature* 384: 184–187, 1996; all of which are incorporated herein by reference.

Amino-terminal-modified chemokines can also be used as vaccine adjuvants. Proteins and glycoproteins injected to induce an immune response must bind to surface of B lymphocytes to stimulate antibody production and must be taken up by antigen presenting cells, processed, and represented to T lymphocytes to mediate a T lymphocyte response. By including with the antigen injection an amino-terminal-modified chemokine the infiltration of the necessary APCs and lymphocytes can be induced by the chemoattractive presence of the chemokine. Potential advantages of using an amino-terminal-modified chemokine is that the amino-terminal-modified chemokine can have an enhanced activity relative to the unmodified chemokine, or have a longer biological half life than the chemokine alone would have.

Amino-terminal-modified chemokines can also be used to enhance the activity of antigen-presenting cells (APCs). The presence of the chemokine domain of the amino-terminal-modified chemokine would chemotactically attract APCs. An antigenic molecule could be attached to the N-terminus of the chemokine for delivery to the APC. When such an antigen-containing amino-terminal-modified chemokine binds to the surface of an APC and is internalized, and the amino-terminal-modified chemokine is degraded within the APC, the antigenic portion of the amino-terminal-modified chemokine would be freed for interaction with MHC proteins and presentation on the surface of the APC.

Amino-terminal-modified chemokines can also be used to affect the chemotactic recruitment of migratory cells. Amino-terminal-modified chemokines may be used to establish a chemoattractive gradient for migratory cells that are expressing the appropriate chemokine receptors, or to obscure an existing chemoattractive gradient. By attaching a large or particularly stable heterologous polypeptide to the amino-terminus of the chemokine, the amino-terminal-modified chemokine will have a longer biological half life and will be able to establish a longer lasting chemoattractive gradient, and will be more effective in obscuring a preexisting gradient. Also, an N-terminal modification may be selected that, by binding to particular molecules or cells, will target the amino-terminal-modified chemokine to a particular site in order to establish a chemoattractive gradient at that site. By altering chemoattractive gradients, amino-terminal-modified chemokines can be used to treat inflammatory and autoimmune disorders that require the recruitment of migratory cells. Also, by attracting to a particular site migratory cells that produce other intercellular factors such as IL-8 or IP-10, amino-terminal-modified chemokines can for example be used to stimulate angiogenesis at that site (if, for example, the recruited migratory cells were secreting IL-8) or to inhibit angiogenesis at that site (if, for example, the recruited migratory cells were secreting IP-10). In addition, by establishing a gradient of amino-terminal-modified chemokine within the bone marrow of a bone marrow transplant recipient, the amino-terminal-modified chemokine can be used to recruit the transplanted bone marrow cells to the bone marrow where they are needed. Similarly, other cellular processes can be affected by amino-terminal-modified chemokines, by using them to attract particular classes of migratory cells secreting determined factors. As another example, bone resorption is controlled by the production within the marrow of soluble regulatory molecules such as IL-1β, IL-6, and TNF-α that mediate osteoclast recruitment, differentiation, and activation. IL-6 influences bone resorption by stimulating the development of osteoclasts from precursor cells and has a mitogenic effect on osteoblasts. An amino-terminal-modified chemokine can be used to attract cells secreting factors that stimulate osteoclasts, or by obscuring an existing chemoattractive gradient can be used to inhibit the recruitment of such cells to a site within bone.

Amino-terminal-modified chemokines can also be used to affect the nature of chemokine-receptor interactions, and may block the binding of endogenous molecules to their receptors. "Receptor functions" that may be affected by N-terminal-modified chemokines include, without limitation, the ability to bind ligand molecules, the ability to interact with other proteins, the ability to generate a "signal" affecting the properties or behaviors of the cell expressing the receptor, or the ability to interact with or affect other cells. By binding to a receptor, amino-terminal-modified chemokines may deliver a signal similar to that received via the normal ligand. The signal delivered by binding the amino-terminal-modified chemokine may have some properties different from that of the normal ligand because of the structure of the amino-terminal-modified chemokine. This could include prolonged triggering/activation or decreased activation. The amino-terminal-modified chemokines, because of their larger size or the nature of the structure of the N-terminal modification, can have a longer half life in vivo compared to unmodified ligand, possibly leading to prolonged signaling/activation. Also the larger size of the amino-terminal-modified chemokine will cause some stearic hindrance which may block the binding of the unmodified ligand. An amino-terminal-modified chemokine can desensitize a receptor's response to normal ligand by binding and inactivating further signaling through the same receptor. In the case where a receptor has more than one signaling function, the amino-terminal-modified chemokine can inhibit one form of signaling while enhancing or altering another. Also, an amino-terminal-modified chemokine can bind to a receptor and cause down regulation and/or internalization of the receptor. Additionally, an amino-terminal-modified chemokine can bind to a receptor and cause the internalization and destruction of the receptor, thus preventing it from recycling to the membrane surface. Also, by binding to one receptor an amino-terminal-modified chemokine can cause another receptor or membrane protein to become desensitized or unable to carry out its normal function.

HIV-1 infection of cells expressing CD4 and the fusin/CXCR4 receptor is greatly decreased by the addition of purified SDF-1 chemokine, which is bound by fusin/CXCR4. Preincubation of cells in the presence of purified SDF-1 for a short period of time at 37° C. causes a profound down-regulation of the receptor. This down-regulation of fusin/CXCR4 correlates with a decrease in the ability of HIV-1 to infect cells. Amino-terminal-modified chemokines can also be used to prevent infection of cells by HIV or other viruses by blocking the binding of virus to chemokine receptors. "HIV molecule" refers to any part of the HIV virus, including isolated polypeptides and fragments thereof, which may or may not be capable of infecting cells susceptible to HIV viral isolates. "HIV particles" refers to HIV virions or derivatives thereof which are capable of infecting certain cell types. As used herein, "susceptible cells" are cell types capable of being infected by certain HIV viral isolates, preferably T1 cells which can be infected by HIV-1$_{IIIB}$. An amino-terminal-modified chemokine is a more effective inhibitor of HIV infection than the corresponding unmodified chemokine when incubation of susceptible cells with the amino-terminal-modified chemokine results in lower incidence of HIV infection, as assayed by the presence of HIV-specific proteins in the cell culture supernatant, than incubation with the unmodified chemokine. For example, Tables 2 and 3 in Example 6 demonstrate that the amino-terminal-modified chemokine met-hSDF-1α, mature human SDF-1α with an additional amino-terminal methionine, is a more effective inhibitor of HIV infection than the corresponding unmodified chemokine lys-hSDF-1α (lysine being the amino-terminal amino acid of the unmodified mature protein).

The amino-terminal-modified chemokine met-hSDF-1α has been shown to bind to cells expressing the fusin/CXCR4 receptor. This binding can block HIV-1 isolates that are T-tropic from infecting fusin-positive cells in multiple ways: competing with HIV for existing chemokine receptors, down-regulation of the chemokine receptors by internalization, as well as desensitization of receptors required by HIV for infection. In a similar manner other amino-terminal-modified chemokines such as met-MIP-1α or met-MIP-1β can bind to cells expressing the CCR5 receptor. This binding will block HIV-1 isolates that are M-tropic from infecting CCR5-positive cells in multiple ways: competing with HIV for existing chemokine receptors, down-regulation of the chemokine receptors by internalization, as well as desensitization of receptors required by HIV for infection. Further modifications of the amino-terminal-modified chemokine, such as changes in glycosylation or additions of chemical moieties to other parts of the amino-terminal-modified chemokine, may result in enhanced binding with loss of signaling, resulting in strong antagonism. By making amino-terminal-modified chemokines with several different chemokines a wide range of chemokine receptors can be inhibited or desensitized, thus blocking viral isolates that have mutated to infect cells using other chemokine receptors. It is also possible to modify a chemokine sequence so that it will bind to a wider array of receptors, for example, by changing the leucine in met-hSDF-1 (at position 27 of SEQ ID NO:s 10 and 11) to a tryosine to change its binding specificity from CXCR receptors to CCR receptors; thus, one modified chemokine could bind to CCR5 as well as other CCR receptors, another modified chemokine could bind to CXCR4 as well as a variety of other CXCR receptors, and yet another could bind to both CCR and CXCR receptors. By simultaneously administering a combination of amino-terminal-modified chemokines, the greatest number of chemokine receptor types could be protected from binding by HIV or other viral isolates.

Amino-terminal-modified chemokines could also interact with the T cell protein CD26 in such a way as to alter the role that CD26 plays in HIV infection.

Administration and Dosing

An amino-terminal-modified chemokine of the present invention (from whatever source derived, including without limitation from recombinant and non-recombinant sources) may be used in a pharmaceutical composition when combined with a pharmaceutically acceptable carrier. Such a composition may also contain (in addition to polypeptide and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, chemokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFNα, IFNβ, TNF0, TNF1, TNF2, G-CSF, Meg-CSF, thrombopoietin, stem cell factor, and erythropoietin. The pharmaceutical composition may further contain other agents which either enhance the activity of the polypeptide or compliment its activity or use in treatment. Such additional factors and/or agents may be included in the pharmaceutical composition to produce a synergistic effect with protein of the invention, or to minimize side effects. Conversely, polypeptides of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A polypeptide of the present invention may be active in multimers (e.g., heterodimers or homodimers) or complexes with itself or other proteins. As a result, pharmaceutical compositions of the invention may comprise a polypeptide of the invention in such multimeric or complexed form.

The pharmaceutical composition of the invention may be in the form of a complex of the polypeptide(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of polypeptide of the present invention is administered to an organism, preferably a mammal, having a condition to be treated. Amino-terminal-modified chemokines of the present invention may be administered in accordance with the method of the invention either alone or in combination with other therapies such as treatments employing cytokines, lymphokines, or other hematopoietic factors. When co-administered with one or more cytokines, lymphokines, or other hematopoietic factors, polypeptides of the present invention may be administered either simultaneously with the cytokine(s), lymphokine(s), other hematopoietic factor (s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

Administration of polypeptides of the present invention used in the pharmaceutical composition or to practice the method of the present invention can be carried out in a variety of conventional ways, such as oral ingestion, inhalation, topical application or cutaneous, subcutaneous, intraperitoneal, parenteral, or intravenous injection. Intravenous administration to the patient is preferred.

When a therapeutically effective amount of polypeptide of the present invention is administered orally, polypeptide of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% polypeptide of the present invention, and preferably from about 25 to 90% polypeptide of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of polypeptide of the present invention, and preferably from about 1 to 50% polypeptide of the present invention.

When a therapeutically effective amount of polypeptide of the present invention is administered by intravenous, cutaneous, or subcutaneous injection, polypeptide of the present invention will be in the form of a pyrogen-free, parenterally acceptable aqueous solution. The preparation of such parenterally acceptable polypeptide solutions, having due regard to pH, isotonicity, stability, and the like, is within the skill in the art. A preferred pharmaceutical composition for intravenous, cutaneous, or subcutaneous injection should contain, in addition to amino-terminal-modified chemokine of the present invention, an isotonic vehicle such as Sodium Chloride Injection, Ringer's Injection, Dextrose Injection, Dextrose and Sodium Chloride injection, Lactated Ringer's Injection, or other vehicle as known in the art. The pharmaceutical composition of the present invention may also contain stabilizers, preservatives, buffers, antioxidants, or other additives known to those of skill in the art.

The amount of polypeptide of the present invention in the pharmaceutical composition of the present invention will depend upon the nature and severity of the condition being treated, and on the nature of prior treatments which the patient has undergone. Ultimately, the attending physician will decide the amount of amino-terminal-modified chemokine of the present invention with which to treat each individual patient. Initially, the attending physician will administer low doses of polypeptide of the present invention and observe the patient's response. Larger doses of polypeptide of the present invention may be administered until the optimal therapeutic effect is obtained for the patient, and at that point the dosage is not increased further. It is contemplated that the various pharmaceutical compositions used to practice the method of the present invention should contain about 0.01 ng to about 100 mg (preferably about 0.1 $\mu$g to about 10 mg, more preferably about 0.1 $\mu$g to about 1 mg) of polypeptide of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the polypeptide of the present invention will be in the range of 12 to 24 hours of continuous intravenous administration. Ultimately the attending physician will decide on the appropriate duration of intravenous therapy using the pharmaceutical composition of the present invention.

Polypeptide of the invention may also be used to immunize animals to obtain polyclonal and monoclonal antibodies which specifically react with the amino-terminal-modified chemokine. Such antibodies may be obtained using either the entire amino-terminal-modified chemokine or fragments thereof as an immunogen, the fragments preferably comprising portions of both the chemokine and the N-terminal modification. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al, FEBS Lett. 211, 10 (1987). Monoclonal antibodies binding to the polypeptide of the invention may be useful diagnostic agents for the immunodetection of the polypeptide. Neutralizing monoclonal antibodies binding to the amino-terminal-modified chemokine may also be useful therapeutics for both conditions associated with the chemokine portion of the amino-terminal-modified chemokine and also in the treatment of some forms of cancer where abnormal expression of that chemokine is involved. In the case of cancerous cells or leukemic cells, neutralizing monoclonal antibodies against the amino-terminal-modified chemokine may be useful in detecting and preventing the metastatic spread of the cancerous cells, which may be mediated by the chemokine corresponding to the chemokine portion of the amino-terminal-modified chemokine.

For compositions of the present invention which are useful for bone, cartilage, tendon, or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage, or tissue damage. Topical administration may be suitable for wound healing and tissue repair. Therapeutically useful agents other than a polypeptide of the invention which may also optionally be included in the composition as described above, may alternatively or additionally be administered simultaneously or sequentially with the composition in the methods of the invention. Preferably for bone and/or cartilage formation, the composition would include a matrix capable of delivering the polypeptide-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance, and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid, and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the amino-terminal-modified chemokine compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the amino-terminal-modified chemokine from the polymer matrix and to provide appropriate handling of the composition, yet not so much that the progenitor cells are prevented from infiltrating the matrix, thereby providing the polypeptide the opportunity to assist the osteogenic activity of the progenitor cells.

In further compositions, polypeptides of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with polypeptides of the present invention.

The dosage regimen of a polypeptide-containing pharmaceutical composition to be used in tissue regeneration will be determined by the attending physician considering various factors which modify the action of the amino-terminal-modified chemokines, e.g., amount of tissue weight desired to be formed, the site of damage, the condition of the damaged tissue, the size of a wound, type of damaged tissue (e.g., bone), the patient's age, sex, and diet, the severity of any infection, time of administration, and other clinical factors. The dosage may vary with the type of matrix used in the reconstitution and with inclusion of other polypeptides in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations, and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of amino-terminal-modified chemokines of the present invention in order to proliferate or to produce a desired effect on or activity in such cells. Treated cells can then be introduced in vivo for therapeutic purposes. For example, stem cells, preferably stem cells that are progenitors of cells susceptible to infection by HIV, can be obtained from an organism to be treated, preferably a human, and transformed ex vivo with polynucleotides of the present invention. When reintroduced into the body, the stem cells will differentiate into particular cell types, or will produce daughter cells that will differentiate into particular cell types, these cell types preferably being cells susceptible to infection by HIV. If the stem cells were transformed with a polynucleotide encoding an amino-terminal-modified chemokine attached to a secretory leader sequence, the differentiated cells can secrete the amino-terminal-modified chemokine which can then bind to chemokine receptors expressed by those differentiated cells or by other cells, protecting the cells from HIV infection.

Patent and literature references cited herein are incorporated by reference as if fully set forth.

The following examples illustrate embodiments of the present invention, but are not intended to limit the scope of the disclosure.

EXAMPLE 1

Expression and Purification of N-Terminal-Modified Chemokines

The amino acid sequences of the full-length human chemokines SDF-1β and SDF-1β (hSDF-1α and hSDF-1β, GenSeq accession numbers R75419 and R75420) are provided as SEQ ID NO:s 1 and 2, respectively, and SEQ ID NO:s 3 and 4 are the nucleotide sequences of cDNA molecules encoding hSDF-1α and hSDF-1β (GeneSeq accession numbers Q74089 and Q74091). The amino acid sequences of the mature hSDF-1α and hSDF-1β proteins begin at amino acid 22 (lysine) in both SEQ ID NO: 1 and SEQ ID NO:2. Polymerase chain reaction (PCR) with hSDF-1α or hSDF-1β cDNA as a template was used to make expression constructs encoding mature hSDF-1α and hSDF-1β proteins, or mature hSDF-1α and hSDF-1β proteins fused to the C-terminus of an expression/purification accessory sequence such as GroHEK (SEQ ID NO:5, AAKDVKHHHHHHGSGSDDDDK). Cloning NdeI/XbaI-restricted hSDF-1α, hSDF-1β, GroHEK/hSDF-1α, and GroHEK/hSDF-1β PCR products (generally referred to) as the hSDF-1PCR products) into the *E. coli* expression vector pAL781 (LaVaile et al., 1993, *Biotechnology* (NY) 11: 187–193) fused the hSDF-1 PCR products in-frame to an ATG codon which serves as the translation initiation codon, producing the four coding sequences shown as SEQ ID NO:6 –SEQ ID NO:9. When hSDF-1α and hSDF-1β are expressed from these vectors, the resulting proteins have a methionine residue attached to the N-terminus of the mature hSDF-1α or hSDF-1β protein; these proteins are referred to as met-hSDF-1 α and met-hSDF-1 β and have the amino acid sequences shown in SEQ ID NO:10 and SEQ ID NO:11, respectively. Similarly, when GroHEK/hSDF-1α and Gro HEK/hSDF-1β are expressed from these vectors, the resulting proteins have the GroHEK peptide attached to the N-terminus of the mature hSDF-1α or hSDF-1β protein, these proteins are referred to as GroHEK/hSDF-1α and GroHEK/hSDF-1β and have the amino acid sequences shown in SEQ ID NO:12 and SEQ ID NO:13, respectively. The expression vectors containing the hSDF-1 PCR products were sequenced and used to transform the *E. coli* strain GI934 (Lu et al., 1996, *J. Biol. Chem.* 271: 5059–5065). The resulting transformed strains hSDF-1α, hSDF-1β, GroHEK/hSDF-1α, and GroHEK/hSDF-1β were deposited with the American Type Culture Collection, P.O. Box 1549, Manassas, Va. 20108 (previously located at 12301 Parklawn Drive, Rockville, Md. 20852) on Aug. 15, 1997 and were given the accession number ATCC 98506, ATCC 98507, ATCC 98508, and ATCC 98509, respectively.

Epression and Purification of met-hSDF-1 and GroHEK/hSDF-1 proteins.

A fresh, overnight culture of GI934 harboring a plasmid expressing met-hSDF-1α, met-hSDF-1β, GroHEK/hSDF-1α, or GroHEK/hSDF-1β was used to inoculate IMC/Amp medium (M9 medium supplemented with 0.2% casamino acids, 0.5% glucose, 1 mM MgSO$_4$, and 100 μg/ml ampicillin) to an OD550 of 0.05. The culture was grown at 30° C. until the OD550 reached 0.5, then L-tryptophan was added to a concentration of 100 μg/ml and the culture temperature shifted to 370° C. Four hours following tryptophan addition the cells were harvested by centrifugation and stored at −80° C. until use.

Cells with inclusion bodies containing met-hSDF-1α, met-hSDF-1β, GroHEK/hSDF-1α, or GroHEK/hSDF-1β proteins were resuspended in 100 mM Tris solution, pH 8, containing 10 mM EDTA, 1 mM p-aminobenzamidine (PABA), and 1 mM phenylmethylsulfonyl fluoride (PMSF) and were lysed in a microfluidizer (Microfluidics, Newton, Mass.) or a French Pressure cell (SLM Instruments, Inc.). After centrifugation of the cell lysate in a GSA rotor at 6000 for 30 minutes, the pellet was washed first with a 100 mM Tris solution, pH 8, containing 1 M NaCl, 1 mM PABA, and 1 mM PMSF, and then with a 100 mM Tris solution, pH 8, containing 0.5% Triton X-100, 1 mM PABA, and 1 mM PMSF.

In order to refold the expressed proteins, washed inclusion bodies were solubilized in 100 ml of a pH 6.5 (or 5.5) solution containing 15 mM sodium phosphate, 15 mM sodium acetate, 1 mM PABA, and 6 M guanidine hydrochloride. After removing the insoluble material, the supernatant was placed in dialysis tubing with a MW cut-off of 5000 for dialysis at 4° C. for 16 hours against a solution containing 15 mM sodium phosphate, 15 mM sodium acetate, 1 mM PABA, and 10 mM EDTA, pH 6.5 (or 5.5). The dialysate containing the refolded met-hSDF-1or GroHEK/hSDF-1proteins was then clarified by centrifugation.

The solution containing refolded met-hSDF-1or GroHEK/hSDF-1proteins was pH-adjusted to 7.5 and loaded on QAE columns equilibrated with a buffer of 15 mM sodium phosphate, pH 7.5. The flow-through of the column was collected and pH-adjusted to 5.5 and loaded onto an SP-650 column equilibrated with a buffer of 15 mM sodium phosphate, 15 mM sodium acetate, pH5.5. The bound material was then eluted with a linear gradient of 1 M NaCl in a buffer of 15 mM sodium phosphate, 15 mM sodium acetate, pH 5.5. The eluate fractions containing the desired hSDF-1 proteins were identified by SDS-PAGE.

Enterokinase Cleavage to Remove the Expression/Purification Accessory Sequence.

Solutions containing purified GroHEK/hSDF-1 proteins are dialyzed against PBS and then cleaved with enterokinase. The digest is loaded on a Ni-IDA column in order to separate the mature hSDF-1 proteins from the enterokinase and GroHEK fragments. Cleavage of the GroHEK peptide from the N-terminus of these GroHEK/hSDF-1α or GroHEK/hSDF-1β proteins produces the mature form of the hSDF-1α or hSDF1β protein having lysine as its N-terminal amino acid; these proteins are referred to as lys-hSDF-1α or lys-hSDF-1β and have the amino acid sequences shown in SEQ ID NO:14 and SEQ ID NO:15, respectively.

EXAMPLE 2

Stimulation of Calcium Flux by N-Terminal-Modified Chemokines

When chemokines bind to receptors present within the membranes of cells, a calcium flux may be induced. When N-terminal-modified chemokines bind to these receptors, the duration, intensity, or other properties of the calcium flux may be altered, or the calcium flux may be inhibited. The calcium fluxes induced by the binding of met-hSDF-1β, lys-hSDF-1β, and lys-hSDF-1α-Fc were measured using the following protocol, and the effects of the binding of mature chemokines (lys-) to chemokine receptors were compared to the effects of binding displayed by N-terminal-modified chemokines (met-). The lys-hSDF-1α-Fc protein (or "chemokine-Fc protein") has the same chemokine N-terminus as a mature hSDF-1α or hSDF-1β protein, but this chemokine domain has been fused to the Fc domain of a human IgG4 molecule so that when expressed the Fc regions interact to form a dimer. This protocol can also be used to assay the calcium flux induced by the interaction of other N-terminal-modified chemkoines with cells containing appropriate chemokine receptors.

U937 cells expressing the appropriate chemokine receptor (fusin/CXCR4) were harvested, washed twice in phenol-red-free RPMI 1640 buffer (10mM HEPES, 0.02% BSA), and adjusted to $10^7$ cells per ml. A 50 μg vial of FLUO-3 ester (Molecular Probes, Eugene, Oreg., catalogue no. F-1242) was dissolved in 50 μl DMSO right before use. 5 μl of this 1 mg/ml FLUO-3 ester solution was added for each ml of cells. The mixture was incubated for 20–30 minutes at room temperature, then washed twice with phenol-red-free RPMI 1640 buffer (phenol-red-free RPMI 1640 with 2.5% fetal calf serum and 10mM HEPES may also be used). The cells were resuspended at $10^7$ per ml in RPMI 1640 buffer and stored on ice until ready to use. To test for calcium flux, 50 μl of cells were diluted to 500 μl with phenol-red-free RPMI 1640 buffer. Using a FACSCAN (BD) fluorescence-activated cell analyzer, the background reading for the loaded cells was determined (FL1 channel). Cells were stimulated appropriately with amino-terminal-modified or unmodified chemokine and read on FACS for 3–15 minutes or more, watching for an increase in fluorescence due to calcium flux. The ionophore ionomycin can be used as a positive control to demonstrate that the cells being tested are capable of demonstrating a calcium flux.

The results of this experiment are shown in FIG. 1, and demonstrate that the binding of met-hSDF-1β to its receptor induces a stronger calcium flux, and at a lower concentration, than either lys-hSDF-1β or lys-hSDF-1α-Fc. This result is surprising in view of the experimental results observed by Wells et at. (1996, *J. Leukoc. Biol.* 59: 53–60), who concluded that the amino-terminal-modified chemokine met-RANTES was unable to induce chemotaxis or calcium mobilization in the RANTES-responsive THP-1 promonocytic cell line.

EXAMPLE 3

Stimulation or Inhibition Chemotaxis by N-Terminal-Modified Chemokines

N-terminal-modified chemokines can be tested for their ability to stimulate or inhibit chemotaxis by any of the following assays for chemotactic activity. These assays (which will identify proteins that induce or prevent chemotaxis) measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed. by J. E. Coligan, A. M. Kruisbeek, D. H. Margulies, E. M. Shevach, W. Strober, Pub. by Greene Publishing Associates and Wiley-Interscience (Chapter 6.12, Measurement of alpha and beta Chemokines 6.12.1–6.12.28); Taub et al., J. Clin. Invest. 95:1370–1376, 1995; Lind et al., APMIS 103:140–146, 1995; Muller et al., Eur. J. Immunol. 25: 1744–1748; Gruber et al., J. of Immunol. 152:5860–5867, 1994; Johnston et al., J. of Immunol. 153: 1762–1768, 1994; all of which are incorporated herein by reference.

EXAMPLE 4

Figure 2:
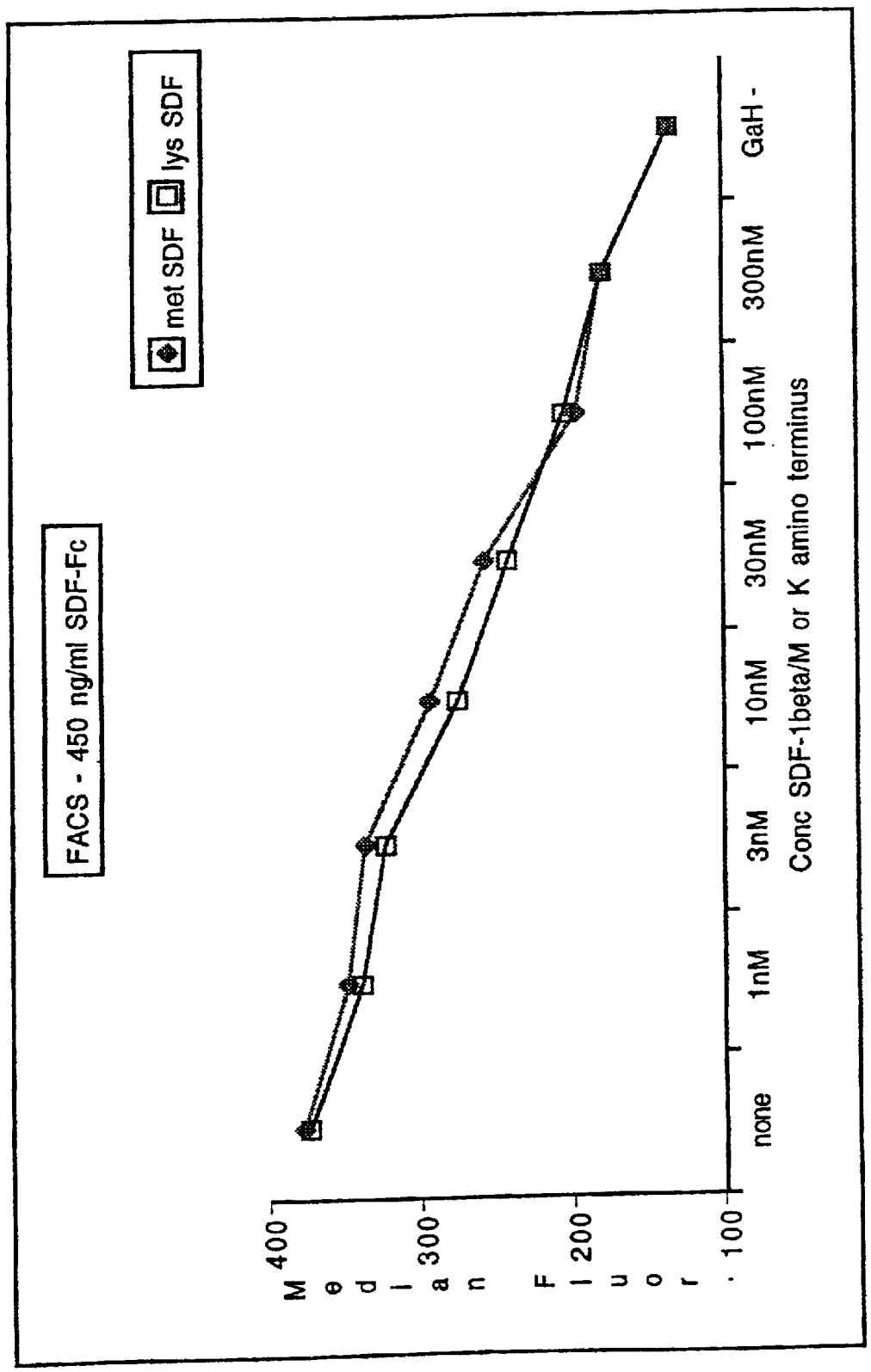
FIG. 2 is a graphical representation of the binding of a chemokine-Fc protein to chemokine receptor after incubation with either N-terminal-modified chemokines or unmodified chemokines, as described in Example 4.

Binding of Chemokine to Receptor After Incubation With N-Terminal-Modified or Unmodified Chemokines The ability of N-terminal-modified and unmodified chemokines to compete with a chemokine-Fc protein for binding to chemokine receptor was tested. Cells were pre-incubated with chemokine and then reacted with chemokine-Fc protein and a fluorescently-labeled anti-Fc antibody to determine if the chemokine-Fc was able to bind the fusin/CXCR4 receptor. As shown in FIG. 2, both the unmodified form and the N-terminal-modified methionine form of hSDF-1β affect the binding of hSDF-1β-Fc with the fusin/CXCR4 receptor.

The ability of the met-hSDF-1β proteins to affect the availability of chemokine receptors for binding was compared to that of mature human SDF-1β proteins having a lysine residue at the N-terminus (lys-hSDF-1β). U937 cells were preincubated with either met-hSDF-1β or lys-hSDF-1β for 1 hour at 4 degrees C. in D-PBS containing 0.02% azide, fetal calf serum, and rabbit serum, followed by incubation with 450 ng/ml lys-hSDF-1α-Fc for 20 minutes on ice, a wash of the cells, and staining with goat anti-human phycoerythrin-conjugated antibody (GaH). After a brief incubation on ice the stained cells are washed and analyzed by fluorescent flow cytometry on a FACSscan machine (BD Instruments, Mountain View, Calif.). Each data point represents the average of two duplicate samples; the "GaH" control shown in FIG. 2 is a sample to which the lys-hSDF-1α-Fc protein was not added. The results of these experiments are shown in FIG. 2, and indicate that both met-hSDF-1β and lys-hSDF-1β can equally block binding of lys-hSDF-1α-Fc to the receptor-expressing cells. It is possible to conclude from this result that the enhanced ability of met-hSDF-1β to inhibit HIV infection (see Example 6 and Tables 2 and 3) is not due to a greater ability to bind the fusin/CXCR4 receptor, since both met-hSDF-1β and lys-hSDF-1β apparently block binding of lys-hSDF-1α-Fc to the receptor to the same extent.

The ability of other N-terminal-modified chemokines to block binding to chemokine receptors is determined by an assay analogous to that described above.

EXAMPLE 5

Down-Modulation of Chemokine Receptor By N-Terminal-Modified Chemokine Binding

Although chemokines can inhibit HIV infection (see Example 6) it has not been established whether this occurs through competition with the virus for the co-receptor binding sites, by making the receptor nonfunctional for HIV binding, or by having altered signaling properties that affect events downstream to infection, i.e. viral replication or production of virus particles. It is possible that binding of the receptor by the chemokine will either cause desensitization or down-modulation (also called "down-regulation"). Chemokine receptors and other seven-span G-protein-coupled receptors can become desensitized: still present on the surface of the cell but no longer able to bind ligand. To investigate this question we have incubated cells with chemokine and then reacted them with a fluorescently-labeled anti-receptor antibody to determine if they still express the receptor. As shown in Table 1, both the unmodified form ("lys-") and the N-terminal-modified ("met-") form of hSDF-1β will down-modulate the fusin/CXCR4 receptor, with the N-terminal-modified met-hSDF-1β demonstrating greater effectiveness in down-modulation.

U937 cells were incubated overnight (for 16 hours) at 37 degrees C. with 500ng/ml of either met-hSDF-1β, lys-hSDF-1β, or lys-hSDF-1α-Fc. Following the incubation the cells were stained with the fluorescently labeled anti-fusin/CXCR4 12G5 monoclonal antibody and analyzed by FACS. The median fluorescence observed using an isotype control, 3.6, was subtracted from the raw fluorescence data to determine the net median fluorescence reported in Table 1. The results of these experiments are shown in Table 1, and indicate that the enhanced ability of met-hSDF-1β to inhibit HIV infection (see Example 6 and Tables 2 and 3), presumably via binding of HIV to the fusin/CXCR4 receptor, could be due to increased down-modulation of the receptor, since met-hSDF-1β causes down-modulation of the receptor to a greater extent than lys-hSDF-1β.

TABLE 1

Down-modulation of fusin/CXCR4 receptors after incubation with N-terminal-modified chemokine (met-hSDF-1β) or chemokines not modified at the N-terminus (lys-hSDF-1β, lys-hSDF-1-Fc).

| Sample: | Median Florescence: | % of Control: |
|---|---|---|
| Control | 23.2 | 100% |
| met-hSDF-1β | 0.5 | 2.3% |
| lys-hSDF-1β | 2.0 | 9.3% |
| lys-hSDF-1-Fc | 2.2 | 9.6% |

Down-regulation of other chemokine receptors by binding of N-terminal-modified chemokines to cells is determined by an assay for receptor down-regulation analogous to that described above.

EXAMPLE 6

Use of N-Terminal-Modified Chemokines to Inhibit HIV Infection of T Cells

The T cell line T1 expresses CD4 and the chemokine receptor fusin/CXCR4, and are readily infected with the T-tropic virus HIV-1$_{IIIB}$. The ability of different forms of hSDF-1β to inhibit HIV binding to the chemokine receptor was tested as follows. T1 cells were preincubated at 37 degrees C. for two hours with a chemokine added at an approximate concentration of 115 nM. The T1 cells were then infected with HIV-1$_{IIIB}$ added at a multiplicity of infection (MOI) of $10^{-2}$. After a four-hour incubation at 37 degrees C., the cells were washed twice and $5\times10^5$ cells per well were added to 24-well plates in 2 ml of medium. Every three days thereafter, half the medium (1 ml) was removed and replaced with 1 ml fresh medium containing approximately 115 nM of the chemokine. Starting on day 4, samples were taken every three days for analysis of HIV-p24 by ELISA. As a control, virus-infected T1 cells were cultured without preincubation or incubation with exogenous chemokine. The lys-hSDF-1α was obtained from PeproTech (Rocky Hill, N.J.). As indicated in Table 2, preincubation with met-hSDF-1β and the readdition of this chemokine to the medium every three days results in near complete inhibition of HIV-1 infection of the T1 CD4+ T cell line. In contrast to the inhibition seen with the N-terminal-modified methionine form of hSDF-1β, the preincubation and addition every three days of approximately 115 nM of the unmodified lys-hSDF-1α or lys-hSDF-1β gives a much lower level of inhibition, about 60% at day 10 of culture. Thus the unmodified hSDF-1α and hSDF-1β having an amino-terminal sequence of KPV . . . (SEQ ID NO:14 and SEQ ID NO:15) appear to give roughly equivalent levels of inhibition of HIV infection, but hSDF-1β with a modified amino-terminal sequence of MKPV . . . (SEQ ID NO:11) gives a level of inhibition of HIV infection (99+% at day 10 of culture) that is three logs greater than that seen with the unmodified chemokines.

TABLE 2

Inhibition of HIV infection of T1 T cells by unmodified (lys-hSDF-1α or β) and N-terminal-modified (met-hSDF-1β) chemokines.

| Chemokine: | HIV-1 p24 (pg/ml) | | | |
|---|---|---|---|---|
| | Day 7: | % Inhibition vs. Control: | Day 10: | % Inhibition vs. Control: |
| Control (no chemokine) | 632 | — | 646,000 | — |
| lys-hSDF-1α | 107 | 83% | 266,000 | 59% |
| lys-hSDF-1β | 160 | 75% | 280,000 | 57% |
| met-hSDF-1β | 5 | 99% | 308 | 99+% |

When T1 cells were cultured for two hours with met-hSDF-1 β before infection with HIV-1$_{IIIB}$ and met-hSDF-1β was not added again, the level of inhibition of infection was 81% at day 5 and 72% at day 10 (Table 3). In this same experiment, culture with met-hSDF-1β followed by addition to culture of this N-terminal-modified chemokine at three-day intervals resulted in complete inhibition of HIV infection. Even when the T cells were not pretreated with N-terminal-modified chemokine before infection with virus, but the met-hSDF-1β was added at 115 nM every three days after infection, the inhibition of infection was 93% at day 5 and 98% at day 10. In contrast, the addition of unmodified chemokine lys-hSDF-1α after infection produced much weaker inhibition of infection (data not shown).

TABLE 3

Inhibition of HIV infection of T1 T cells by pre-treatment and post-treatment with N-terminal-modified (met-hSDF-1β) chemokines.

| | % Inhibition vs. Control | |
|---|---|---|
| Treatment with N-terminal Modified Chemokine met-SDF-1β: | Day 5: | Day 10: |
| Control (no chemokine) | — | — |
| Pretreatment only | 81% | 72% |
| Pretreatment and addition every 3rd day | 99.9% | 99.9% |
| No pretreatment, addition every 3rd day | 93% | 98% |

The results shown in Tables 2 and 3 are surprising in view of the experimental results observed by Simmons et al. in testing the ability of the amino-terminal-modified chemokine met-RANTES to inhibit HIV-1 infection of peripheral blood mononuclear cells or primary macrophage cultures (1997, *Science* 276: 276–279). Simmons et al. found that met-RANTES was either about as effective or less effective in inhibiting HIV-1 infection of these cells than the unmodified RANTES chemokine.

What is claimed is:

1. A composition comprising an isolated polynucleotide encoding an amino-terminal-modified chemokine, wherein the amino-terminal-modified chemokine comprises at least one methionine, at least one aminooxypentane residue, or at least one GroHEK peptide covalently attached to the amino terminus of the chemokine, and wherein the polynucleotide is selected from the group consisting of:
   (a) a polynucleotide comprising the nucleotide sequence of SEQ ID NO:6;
   (b) a polynucleotide comprising the nucleotide sequence of the protein-coding sequence of the polynucleotide encoding met-hDSF-1α deposited under accession number ATCC 98506;
   (c) a polynucleotide encoding an amino-terminal-modified chemokine comprising the amino acid sequence of SEQ ID NO:10;
   (d) a polynucleotide encoding a protein comprising an amino-terminal fragment of the amino acid sequence of SEQ ID NO: 10;
   (e) a polynucleotide comprising a nucleotide sequence complementary to any one of the polynucleotides specified in (a)–(d) above; and
   (f) a polynucleotide capable of hybridizing at either (i) 4×SSC at 65° C. or (ii) 50% formamide and 4×SSC at 42° C., to any one of the polynucleotides specified in (a)–(e) above.

2. A composition comprising an isolated polynucleotide encoding an amino-terminal-modified chemokine, wherein the amino-terminal-modified chemokine comprises at least one methionine, at least one aminooxypentane residue, or at least one GroHEK peptide covalently attached to the amino terminus of the chemokine, and wherein the polynucleotide is selected from the group consisting of:
   (a) a polynucleotide comprising the nucleotide sequence of SEQ ID NO:7;
   (b) a polynucleotide comprising the nucleotide sequence of the protein-coding sequence of the polynucleotide encoding met-hDSF-1β deposited under accession number ATCC 98506;
   (c) a polynucleotide encoding an amino-terminal-modified chemokine comprising the amino acid sequence of SEQ ID NO: 11;
   (d) a polynucleotide encoding a protein comprising an amino-terminal fragment of the amino acid sequence of SEQ ID NO: 11;

(e) a polynucleotide comprising a nucleotide sequence complementary to any one of the polynucleotides specified in (a)–(d) above; and (f) a polynucleotide capable of hybridizing at either (i) 4×SSC at 65° C. or (ii) 50% formamide and 4×SSC at 42° C., to any one of the polynucleotides specified in (a)–(e) above.

3. A composition comprising an isolated polynucleotide encoding an amino-terminal-modified chemokine, wherein the amino-terminal-modified chemokine comprises at least one methionine, at least one aminooxypentane residue, or at least one GroHEK peptide covalently attached to the amino terminus of the chemokine, and wherein the polynucleotide is selected from the group consisting of:

(a) a polynucleotide comprising the nucleotide sequence of SEQ ID NO:8;

(b) a polynucleotide comprising the nucleotide sequence of the protein-coding sequence of the polynucleotide encoding GroHEK/hSDF-1α deposited under accession number ATCC 98508;

(c) a polynucleotide encoding an amino-terminal-modified chemokine comprising the amino acid sequence of SEQ ID NO: 12;

(d) a polynucleotide encoding a protein comprising an amino-terminal fragment of the amino acid sequence of SEQ ID NO: 12;

(e) a polynucleotide comprising a nucleotide sequence complementary to any one of the polynucleotides specified in (a)–(d) above; and (f) a polynucleotide capable of hybridizing at either (i) 4×SSC at 65° C. or (ii) 50% formamide and 4×SSC at 42° C., to any one of the polynucleotides specified in (a)–(e) above.

4. A composition comprising an isolated polynucleotide encoding an amino-terminal-modified chemokine, wherein the amino-terminal-modified chemokine comprises at least one methionine, at least one aminooxypentane residue, or at least one GroHEK peptide covalently attached to the amino terminus of the chemokine, and wherein the polynucleotide is selected from the group consisting of:

(a) a polynucleotide comprising the nucleotide sequence of SEQ ID NO:9;

(b) a polynucleotide comprising the nucleotide sequence of the protein-coding sequence of the polynucleotide encoding GroHEK/hSDF-l1β deposited under accession number ATCC 98509;

(c) a polynucleotide encoding an amino-terminal-modified chemokine comprising the amino acid sequence of SEQ ID NO:13;

(d) a polynucleotide encoding a protein comprising an amino-terminal fragment of the amino acid sequence of SEQ ID NO: 13;

(e) a polynucleotide comprising a nucleotide sequence complementary to any one of the polynucleotides specified in (a)–(d) above; and (f) a polynucleotide capable of hybridizing at either (i) 4×SSC at 65° C. or (ii) 50% formamide and 4×SSC at 42° C., to any one of the polynucleotides specified in (a)–(e) above.

* * * * *

UNITED STATES PATENT AND TRADEMARK OFFICE
CERTIFICATE OF CORRECTION

PATENT NO. : 6,852,508 B1
DATED : February 8, 2005
INVENTOR(S) : Stephen H. Herrmann et al.

It is certified that error appears in the above-identified patent and that said Letters Patent is hereby corrected as shown below:

Column 42,
Lines 47 and 48, part (f), delete "C." and insert -- C --.
Line 61, delete "98506" and insert -- 98507 --.

Column 43,
Lines 5 and 6, part (f), delete "C." and insert -- C --.
Line 32, part (f), delete "C." and insert -- C --.

Column 44,
Line 1, part (f), delete "C." and insert -- C --.
Lines 28 and 29, part (f), delete "C." and insert -- C --.

Signed and Sealed this

Seventeenth Day of May, 2005

JON W. DUDAS
*Director of the United States Patent and Trademark Office*